United States Patent
Leonard et al.

(10) Patent No.: US 9,328,095 B2
(45) Date of Patent: *May 3, 2016

(54) HETEROARYL LINKED QUINOLINYL MODULATORS OF RORGAMMAT

(71) Applicant: Janssen Pharmaceutica NV, Beerse (BE)

(72) Inventors: Kristi A. Leonard, Lansdale, PA (US); Kent Barbay, Flourtown, PA (US); James P. Edwards, San Diego, CA (US); Kevin D. Kreutter, Plainsboro, NJ (US); David A. Kummer, San Diego, CA (US); Umar Maharoof, North Wales, PA (US); Rachel Nishimura, San Diego, CA (US); Maud Urbanski, Flemington, NJ (US); Hariharan Venkatesan, San Diego, CA (US); Aihua Wang, Jamison, PA (US); Ronald L. Wolin, San Diego, CA (US); Craig R. Woods, San Diego, CA (US); Maxwell D. Cummings, Ambler, PA (US)

(73) Assignee: JANSSEN PHARMACEUTICA NV

( * ) Notice: Subject to any disclaimer, the term of this patent is extended or adjusted under 35 U.S.C. 154(b) by 0 days.

This patent is subject to a terminal disclaimer.

(21) Appl. No.: 14/053,736

(22) Filed: Oct. 15, 2013

(65) Prior Publication Data

US 2015/0105365 A1 Apr. 16, 2015

(51) Int. Cl.
| | |
|---|---|
| *A61K 45/06* | (2006.01) |
| *C07D 401/14* | (2006.01) |
| *C07D 401/12* | (2006.01) |
| *A61K 31/4709* | (2006.01) |

(52) U.S. Cl.
CPC .......... *C07D 401/14* (2013.01); *A61K 31/4709* (2013.01); *A61K 45/06* (2013.01); *C07D 401/12* (2013.01)

(58) Field of Classification Search
None
See application file for complete search history.

(56) References Cited

U.S. PATENT DOCUMENTS

| | | | |
|---|---|---|---|
| 3,472,859 | A | 10/1969 | Lesher |
| 4,656,283 | A | 4/1987 | Doehner, Jr. |
| 4,710,507 | A | 12/1987 | Campbell et al. |
| 4,910,327 | A | 3/1990 | Doehner, Jr. |
| 4,927,926 | A | 5/1990 | Corominas et al. |
| 5,409,930 | A | 4/1995 | Spada et al. |
| 5,780,634 | A | 7/1998 | Inoue et al. |
| 6,248,739 | B1 | 6/2001 | Turner et al. |
| 6,451,812 | B1 | 9/2002 | End et al. |
| 6,624,159 | B2 | 9/2003 | Anderson et al. |
| 6,686,356 | B2 | 2/2004 | Strohbach et al. |
| 6,743,805 | B2 | 6/2004 | End et al. |
| 7,652,014 | B2 | 1/2010 | Mabire et al. |
| 7,902,225 | B2 | 3/2011 | Guillemont et al. |
| 8,017,606 | B2 | 9/2011 | Andries et al. |
| 8,389,739 | B1 | 3/2013 | Thacher et al. |
| 2003/0166675 | A1 | 9/2003 | Yang |
| 2005/0131014 | A1 | 6/2005 | Collini et al. |
| 2007/0072844 | A1 | 3/2007 | Jones et al. |
| 2008/0188521 | A1 | 8/2008 | Grimm et al. |
| 2009/0197859 | A1 | 8/2009 | Collantes et al. |
| 2009/0286829 | A1 | 11/2009 | Heidelbaugh et al. |
| 2010/0311760 | A1 | 12/2010 | de Vicente Fidalgo et al. |
| 2012/0322837 | A1 | 12/2012 | Maeba et al. |
| 2014/0107096 | A1* | 4/2014 | Leonard et al. .......... 514/210.21 |

FOREIGN PATENT DOCUMENTS

| | | |
|---|---|---|
| CN | 101143845 | 3/2008 |
| CN | 101899011 | 12/2010 |
| EP | 371564 A2 | 6/1990 |
| EP | 709377 A1 | 5/1996 |
| EP | 1106612 A1 | 6/2001 |
| EP | 2368886 A1 | 9/2011 |
| GB | 2095668 A | 10/1982 |

(Continued)

OTHER PUBLICATIONS

U.S. Appl. No. 14/053,682.
U.S. Appl. No. 14/053,773.
U.S. Appl. No. 14/053,797.
U.S. Appl. No. 14/053,906.
U.S. Appl. No. 14/053,653.
U.S. Appl. No. 14/053,707.
International Search Report—PCT/US2013/065007, Jan. 7, 2014.
International Search Report—PCT/US2013/065013, Dec. 16, 2013.
International Search Report—PCT/US2013/065031, Dec. 13, 2013.
International Search Report—PCT/US2013/065040, Dec. 16, 2013.
International Search Report—PCT/US2013/065048, Dec. 3, 2013.
International Search Report—PCT/US2013/065053, Jan. 7, 2014.
International Search Report—PCT/US2013/065026, Feb. 21, 2014.

(Continued)

*Primary Examiner* — San-Ming Hui
*Assistant Examiner* — Andrew Lee
(74) *Attorney, Agent, or Firm* — Yuriy P. Stercho

(57) ABSTRACT

The present invention comprises compounds of Formula I.

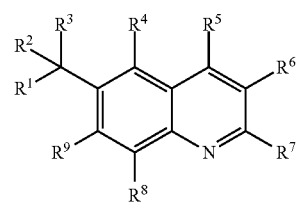

Formula I wherein:
$R^1$, $R^2$, $R^3$, $R^4$, $R^5$, $R^6$, $R^7$ $R^8$, and $R^9$ are defined in the specification.

The invention also comprises a method of treating or ameliorating a syndrome, disorder or disease, wherein said syndrome, disorder or disease is rheumatoid arthritis or psoriasis. The invention also comprises a method of modulating RORγt activity in a mammal by administration of a therapeutically effective amount of at least one compound of claim 1.

5 Claims, No Drawings

(56) References Cited

FOREIGN PATENT DOCUMENTS

| | | |
|---|---|---|
| JP | 48026772 | 4/1973 |
| WO | WO 9718208 A1 | 5/1997 |
| WO | WO 9721701 A1 | 6/1997 |
| WO | WO 9744339 A1 | 11/1997 |
| WO | WO 9855124 A1 | 12/1998 |
| WO | WO 9932450 A1 | 7/1999 |
| WO | WO 9950660 A1 | 10/1999 |
| WO | WO 0001386 A1 | 1/2000 |
| WO | WO 0001411 A1 | 1/2000 |
| WO | WO 0001714 A1 | 1/2000 |
| WO | WO 0039082 A2 | 7/2000 |
| WO | WO 0040561 A1 | 7/2000 |
| WO | WO 0040563 A1 | 7/2000 |
| WO | WO 0047574 A1 | 8/2000 |
| WO | WO 0156552 A2 | 8/2001 |
| WO | WO 0162234 A2 | 8/2001 |
| WO | WO 0164194 A2 | 9/2001 |
| WO | WO 0164195 A2 | 9/2001 |
| WO | WO 0164196 A2 | 9/2001 |
| WO | WO 0164197 A2 | 9/2001 |
| WO | WO 0164198 A2 | 9/2001 |
| WO | WO 0164199 A2 | 9/2001 |
| WO | WO 0164217 A2 | 9/2001 |
| WO | WO 0164218 A2 | 9/2001 |
| WO | WO 0164226 A2 | 9/2001 |
| WO | WO 0164246 A2 | 9/2001 |
| WO | WO 0164252 A2 | 9/2001 |
| WO | WO 0202558 A1 | 1/2002 |
| WO | WO 0204445 A1 | 1/2002 |
| WO | WO 0204462 A1 | 1/2002 |
| WO | WO 0224682 A1 | 3/2002 |
| WO | WO 0224686 A2 | 3/2002 |
| WO | WO 0224687 A1 | 3/2002 |
| WO | WO 0228837 A1 | 4/2002 |
| WO | WO 0243733 A1 | 6/2002 |
| WO | WO 02051835 A1 | 7/2002 |
| WO | WO 02064142 A1 | 8/2002 |
| WO | WO 0270487 A1 | 9/2002 |
| WO | WO 02085364 A1 | 10/2002 |
| WO | WO 03/000705 | 1/2003 |
| WO | WO 03053971 A1 | 7/2003 |
| WO | WO 03053972 A1 | 7/2003 |
| WO | WO 03082350 A2 | 10/2003 |
| WO | WO 2004019932 A1 | 3/2004 |
| WO | WO 2004024693 A1 | 3/2004 |
| WO | WO 2004037792 A2 | 5/2004 |
| WO | WO 2005054201 A1 | 6/2005 |
| WO | WO 2005054210 A1 | 6/2005 |
| WO | WO 2005058843 A1 | 6/2005 |
| WO | WO 2005070430 A1 | 8/2005 |
| WO | WO 2005075428 A1 | 8/2005 |
| WO | WO 2006003146 A1 | 1/2006 |
| WO | WO 2006013896 A1 | 2/2006 |
| WO | WO 2006025683 | 3/2006 |
| WO | WO 2006052718 A2 | 5/2006 |
| WO | WO 2007014940 A2 | 2/2007 |
| WO | WO 2007014941 A2 | 2/2007 |
| WO | WO 2007088978 A1 | 8/2007 |
| WO | WO 2008051805 A2 | 5/2008 |
| WO | WO 2008068267 A1 | 6/2008 |
| WO | WO 2008098104 A8 | 8/2008 |
| WO | WO 2008112525 A2 | 9/2008 |
| WO | WO 2008144767 A1 | 11/2008 |
| WO | WO 2009091735 A1 | 7/2009 |
| WO | WO 2009140138 A1 | 11/2009 |
| WO | WO 2010068296 A1 | 6/2010 |
| WO | WO 2010127208 A1 | 11/2010 |
| WO | WO 2010151740 A4 | 12/2010 |
| WO | WO 2011020861 A1 | 2/2011 |
| WO | WO 2011112264 A1 | 9/2011 |
| WO | WO 2011130707 A2 | 10/2011 |
| WO | WO 2012064744 A2 | 5/2012 |
| WO | WO 2012116137 A2 | 8/2012 |
| WO | WO 2012158784 A2 | 11/2012 |
| WO | WO 2013061074 A1 | 5/2013 |
| WO | WO 2013064231 A1 | 5/2013 |
| WO | WO 2013079223 A1 | 6/2013 |

OTHER PUBLICATIONS

Codarri, "RoRγt Drives Production of the Cytokine GM-CSF in Helper T Cells, Which is Essential for the Effector Phase of Autoimmune Neuroinflammation", Nature Immunology, vol. 12(16), Jun. 2011, pp. 560-568.

Bink A, (A fungicidal piperazine-1-carboxamidine induces mitochondrial fission-dependent apoptosis in yeast), FEMS Yeast Research (2010), 10(7), 812-818.

Nieman J, (Modifications of C-2 on the pyrroloquinoline template aimed at the development of potent herpes virus antivirals with improved aqueous solubility), Bioorganic & Medicinal Chemistry Letters (2010), 20(10), 3039-3042.

Tanis S, (The design and development of 2-aryl-2-hydroxy ethylamine substituted 1H,7H-pyrido[1,2,3-de]quinoxaline-6-carboxamides as inhibitors of human cytomegalovirus polymerase), Bioorganic & Medicinal Chemistry Letters (2010), 20(6), 1994-2000.

Mao D, (Synthesis and Na+/H+ Exchanger-1 Inhibitory Activity of Substituted (Quinolinecarbonyl)guanidine Derivatives), Chemistry & Biodiversity (2009), 6(10), 1727-1736.

Sato M, (Quinolone Carboxylic Acids as a Novel Monoketo Acid Class of Human Immunodeficiency Virus Type 1 Integrase Inhibitors), Journal of Medicinal Chemistry (2009), 52(15), 4869-4882.

Aghera V, (Synthesis, spectral and microbial studies of some novel quinoline derivatives via Vilsmeier-Haack reagent) Journal; (online computer file) URL: http://www.arkat-usa.org/get-file/25177/.

Inada T, (One-step synthesis of ethyl quinaldates by Lewis acid-catalyzed three-component coupling reaction of aromatic amines, aliphatic aldehydes, and ethyl glyoxylate), Heterocycles (2005), 66, 611-619.

Zelenin A, (Reaction of polyfluoro carbonyl compounds with 1,2,3,4-tetrahydroquinoline), Izvestiya Akademii Nauk SSSR, Seriya Khimicheskaya (1986), (9), 2074-80 Abstract Only.

Hirao I, (Studies on the synthesis of quinoline compounds. I. Syntheses of 3,3'-dicarboxy-1,1'-diethyl-4,4'-dioxo-1,1',4,4'-tetrahydrobiquinolines), Memoirs of the Kyushu Institute of Technology, Engineering (1984), 14, 13-16.

Abdul-Ahad P, (Trends in dehydrogenase inhibitory potencies of some quinolones, using quantum chemical indices), European Journal of Medicinal Chemistry (1982), 17(4), 301-6.

Baker B, (Irreversible enzyme inhibitors. 191. Hydrophobic bonding to some dehydrogenases by 6-, 7-, or 8-substituted-4-hydroxyquinoline-3-carboxylic acids), Journal of Medicinal Chemistry (1972), 15(3), 235-7.

Ramachary D, (A novel and green protocol for two-carbon homologation: a direct amino acid/K2CO3-catalyzed four-component reaction of aldehydes, active methylenes, Hantzsch esters and alkyl halides), Tetrahedron Letters (2006) 47, 651-656.

Dong C, (Diversification of T-helper-cell lineages: finding the family root of IL-17-producing cells), Nat Rev Immunol (2006), 6(4), 329-333.

McKenzie B, (Understanding the IL-23-IL-17 immune pathway), Trends Immunol (2006), 27(1), 17-23.

Ivanov II B, (The orphan nuclear receptor RORgammat directs the differentiation program of proinflammatory IL-17+ T helper cells), Cell (2006), 126(6), 1121-33.

Cua, D (Interleukin-23 rather than interleukin-12 is the critical cytokine for autoimmune inflammation of the brain), Nature (2003), 421(6924), 744-748.

Langrish C, (IL-23 drives a pathogenic T cell population that induces autoimmune inflammation), J Exp Med (2005), 201(2), 233-240.

Tonel G, (Cutting edge: A critical functional role for IL-23 in psoriasis), J Immunol (2010), 185(10), 5688-5691.

Barczyk A, (Interleukin-17 in sputum correlates with airway hyperresponsiveness to methacholine), Respir Med (2003), 97(6), 726-733.

(56) References Cited

OTHER PUBLICATIONS

Lock C, (Gene-microarray analysis of multiple sclerosis lesions yields new targets validated in autoimmune encephalomyelitis) Nat Med (2002), 8(5), 500-8.
Papp K, (Brodalumab, an anti-interleukin-17-receptor antibody for psoriasis), N Engl J Med (2012), 366(13), 1181-1189.
Leonardi C, (Anti-interleukin-17 monoclonal antibody ixekizumab in chronic plaque psoriasis), N Engl J Med (2012), 366(13), 1190-1199.
Hueber W, (Effects of AIN457, a fully human antibody to interleukin-17A, on psoriasis, rheumatoid arthritis, and uveitis), Sci Transl Med (2010), 2, 5272.
Gao W, (Clean and Convienient One-Pot Synthesis of 4-Hydroxycoumarin and 4-Hydroxy-2-Quinolone Derivatives), Synthetic Communications (2010) 40, 732-738.
Moriarty R, Organic Reactions (2001), 57, 327-415.
Pongratz E, et al., (Ylide von Heterocyclen, VIII Reaktionen von Iodonium-Yliden mit Säuren), Monatshefte fur Chemie (1984) 115(2), 231-242.
Osborne A, (Regioselective Al koxydehalogenation of 2,4- Di halogenoquinolines and a Reinvestigation of the Bromination of 2-Methoxyquinoline), J Chem Soc Perkin Trans 1 (1993), 181-184.
Osborne A, (Further studies of regioselective alkoxydehalogenation of 2,4-dichloroquinolines, 2,6-dichloropyridine and 2,4-dichloronitrobenzene), J Chem Research (S) (2002), 4.
Ramachary D, (Development of Pharmaceutical Drugs, Drug Intermediates and ingredients by Using Direct Organo-Click Reactions), Eur. J. Org. Chem. (2008), 975-993.
Korn T, (IL-17 and Th17 Cells), Annual Reviews of Immunology (2009), 27, 485-517.
Kolls J, (Interleukin-17 family members and inflammation), Immunity (2004), 21(4), 467-476.
Stamp L, (Interleukin-17: the missing link between T-cell accumulation and effector cell actions in rheumatoid arthritis), Immunol Cell Biol (2004), 82(1), 1-9.
Kamenecka T, (Synthetic modulators of the retinoic acid receptor-related orphan receptors), Med Chem Commun (2013), 4, 764-776.
Yen D, (IL-23 is essential for T cell-mediated colitis and promotes inflammation via IL-17 and IL-6), J Clin Invest (2006), 116(5), 1310-1316.
Fujino S, (Increased expression of interleukin 17 in inflammatory bowel disease) Gut (2003), 52(1), 65-70.
Krueger J, (IL-17A is essential for cell activation and inflammatory gene circuits in subjects with psoriasis) J Allergy Clin Immunol (2012), 130(1), 145-154.
Nunez C, (IL23R: a susceptibility locus for celiac disease and multiple sclerosis?) Genes Immun (2008), 9(4), 289-93.
Bowes J, (The genetics of psoriatic arthritis: lessons from genome-wide association studies), Discov Med (2010), 10(52), 177-83.
Kochi Y, (A regulatory variant in CCR6 is associated with rheumatoid arthritis susceptibility), Nat Genet (2010), 42(6), 515-9.
Garber K, (Psoriasis: from bed to bench and back), Nat Biotech (2011), 29, 563-566.
Madrid P, et al. (Synthesis of ring-substituted 4-aminoquinolines and evaluation of their antimalarial activities), Bioorganic & Medicinal Chemistry Letters (2005), 15, 1015-1018.
Gore T, (Synthesis of substituted 6,6'-biquinolines from ethyl ethoxy-methyleneacetoacetate), Indian Journal of Chemistry (1965), 3(2), 90-1.
Gazouli, M, (NOD2/CARD15, ATG16L1 and IL23R gene polymorphisms and childhood-onset of Crohn's disease) World J. Gastroenterol (2010) 16(14), 1753-8.
Knochel P, (Preparation of Polyfunctional Ketones by a Cobalt(II) Mediated Carbonylation of Organozinc Reagents), Tetrahedron Letters (1995), 36(46), 8411-8414.
Dorwald F. A. "SLIDE Reactions in Organic Synthesis", 2005, Wiley: VCH, Weinheim p. IX of Preface p. 1-15.
Venkatesh, et al. "Role of the Development Scientist in Compound Lead Selection and Optimization", J. Pharm. Sci. vol. 89, No. 2, pp. 145-154 2000.
Hiro, STN Document No. 102: 149081 Abstract of Memoirs of the Kyushu Institute of Technology, Engineering (1984), vol. 14, pp. 13-16.
STN Search Report Mar. 12, 2015, RN 1 347913-41-0.
U.S. Appl. No. 14/513,426.
U.S. Appl. No. 14/513,455.
International Search Report—PCT/US2014/60372, Mar. 27, 2015.
International Search Report—PCT/US2014/60375, Mar. 26, 2015.
U.S. Appl. No. 14/053,653, Office Action dated Sep. 15, 2014.
U.S. Appl. No. 14/053,653, Notice of Allowance dated Mar. 30, 2015.
U.S. Appl. No. 14/053,682, Office Action dated Sep. 12, 2014.
U.S. Appl. No. 14/053,682, Notice of Allowance dated Sep. 12, 2014.
U.S. Appl. No. 14/053,707, Office Action dated Sep. 11, 2014.
U.S. Appl. No. 14/053,707, Notice of Allowance dated Sep. 11, 2014.
U.S. Appl. No. 12/053,736, Office action dated Mar. 26, 2015.
U.S. Appl. No. 14/053,736, Office Action dated Oct. 3, 2014.
U.S. Appl. No. 14/053,773, Office Action dated Apr. 6, 2015.
U.S. Appl. No. 14/053,773, Office Action dated Jan. 9, 2015.
U.S. Appl. No. 14/053,797, Office Action dated Sep. 12, 2014.
U.S. Appl. No. 14/053,797, Notice of Allowance Apr. 7, 2015.
U.S. Appl. No. 14/513,426, Office Action dated Apr. 16, 2015.
U.S. Appl. No. 14/513,455, Office Action dated Apr. 28, 2015.
U.S. Appl. No. 14/053,906, Office Action dated Sep. 12, 2004.
U.S. Appl. No. 14/053,906, Notice of Allowance dated Mar. 23, 2015.

* cited by examiner

HETEROARYL LINKED QUINOLINYL MODULATORS OF RORGAMMAT

FIELD OF THE INVENTION

The invention is directed to substituted quinoline compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of CD4+ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517.), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23.). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor ROR-gammat directs the differentiation program of proinflammatory IL-17+ T helper cells." Cell 126(6): 1121-33.). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8. ; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6.). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33.; Fujino, S., A. Andoh, et al. (2003). "Increased expression of interleukin 17 in inflammatory bowel disease." Gut 52(1): 65-70; Lock, C., G. Hermans, et al. (2002). "Gene-microarray analysis of multiple sclerosis lesions yields new targets validated in autoimmune encephalomyelitis." Nat Med 8(5): 500-8.; Krueger, J. G., S. Fretzin, et al. "IL-17A is essential for cell activation and inflammatory gene circuits in subjects with psoriasis." J Allergy Clin Immunol 130(1): 145-154 e9.). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8, Nunez, C., B. Dema, et al. (2008). "IL23R: a susceptibility locus for celiac disease and multiple sclerosis?" Genes Immun 9(4): 289-93; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9.). Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9; Leonardi, C., R. Matheson, et al. "Anti-interleukin-17 monoclonal antibody ixekizumab in chronic plaque psoriasis." N Engl J Med 366(13): 1190-9.). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.).

All the above evidence supports inhibition of the Th17 pathway by modulating RORγt activity as an effective strategy for the treatment of immune-mediated inflammatory diseases.

SUMMARY OF THE INVENTION

The present invention comprises compounds of Formula I.

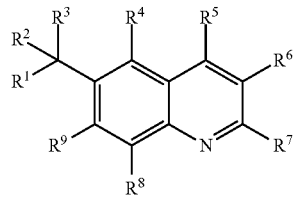

Formula I wherein:

R¹ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, $C(O)CH_3$, $C(O)NH_2$, $CH_3$, $CH_2CH_3$, $CF_3$, Cl, F, —CN, $OCH_3$, $N(CH_3)_2$, —$(CH_2)_3OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups; and wherein said azetidinyl is optionally substituted with $CO_2C(CH_3)_3$, $C(O)NH_2$, $CH_3$, $SO_2CH_3$, or $C(O)CH_3$;

R² is 1-methyl-1,2,3-triazolyl, pyridyl, pyridyl-N-oxide, 1-methyl pyrazol-4-yl, pyrimidin-5-yl, pyridazyl, pyrazin-2-yl, oxazolyl, isoxazolyl, N-acetyl-azetidin-3-yl, N-methylsulfonyl-azetidin-3-yl, N-Boc-azetidin-3-yl, N-methyl-azetidin-3-yl, N-acetamidyl-azetidin-3-yl, N-acetyl piperidinyl, 1-H-piperidinyl, N-Boc-piperidinyl, N—$C_{(1-2)}$alkyl-piperidinyl, thiazol-5-yl, 1-(3-methoxypropyl)-imidazol-5-yl, or 1-$C_{(1-2)}$alkyl imidazol-5-yl; wherein said 1-$C_{(1-2)}$alkyl imidazol-5-yl is optionally substituted with up to two additional $CH_3$ groups, or one substituent selected from the group consisting of $SCH_3$, and Cl; and said pyridyl, and pyridyl-N-oxide are optionally substituted with up to two substituents independently selected from the group consisting of $C(O)NH_2$, —CN, $OCH_3$, $CF_3$, Cl, and $CH_3$; and said thiazol-5-yl, oxazolyl, and isoxazolyl are optionally substituted with up to two $CH_3$ groups; and said 1-methyl pyrazol-4-yl is optionally substituted with up to two additional $CH_3$ groups;

R³ is H, OH, $OCH_3$, $NHCH_3$, $N(CH_3)_2$, or $NH_2$;

R⁴ is H, or F;

R⁵ is H, Cl, —CN, $CF_3$, $SCH_3$, $OC_{(1-3)}$alkyl, OH, $C_{(1-4)}$alkyl, $N(CH_3)OCH_3$, $NH(C_{(1-2)}$alkyl), $N(C_{(1-2)}$alkyl)$_2$, NH-cyclopropyl, $OCHF_2$, 4-hydroxy-piperidinyl, azetidin-1-yl, or fur-2-yl;

R⁶ is —O-phenyl, —NHphenyl, —N($C_{(1-3)}$alkyl)phenyl, —N($CO_2C(CH_3)_3$)phenyl, —O-pyridyl, —NHpyridyl, —N($C_{(1-3)}$alkyl)pyridyl, or —N($CO_2C(CH_3)_3$)pyridyl wherein said phenyl portions thereof or said pyridyl portions thereof are optionally substituted with $OCF_3$, $SO_2CH_3$, $CF_3$, $CHF_2$, imidazol-1-yl, pyrazol-1-yl, 1,2,4-triazol-1-yl, $CH_3$, $OCH_3$, Cl, F, or —CN;

R⁷ is H, Cl, —CN, $C_{(1-4)}$alkyl, $OCH_2CF_3$, $OCH_2CH_2OCH_3$, $CF_3$, $SCH_3$, $SO_2CH_3$, $OCHF_2$, $NA^1A^2$, $C(O)NHCH_3$, $N(CH_3)CH_2CH_2NA^1A^2$, $OCH_2CH_2NA^1A^2$, $OC_{(1-3)}$alkyl, $OCH_2$-(1-methyl)-imidazol-2-yl, imidazol-2-yl, fur-2-yl, pyrazol-4-yl, pyrid-3-yl, or pyrimidin-5-yl; thiophen-3-yl, 1-methyl-indazol-5-yl, 1-methyl-indazol-6-yl, phenyl, or

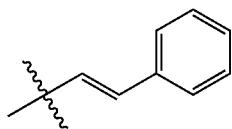

wherein said imidazolyl or pyrazolyl can be optionally substituted with a $CH_3$ group;

A¹ is H or $C_{(1-4)}$alkyl;

A² is H, $C_{(1-4)}$alkyl, cyclopropyl, $C_{(1-4)}$alkyl$OC_{(1-4)}$alkyl, $C_{(1-4)}$alkylOH, $C(O)C_{(1-2)}$alkyl, or $OCH_3$; or A¹ and A² may be taken together with their attached nitrogen to form a ring selected from the group consisting of:

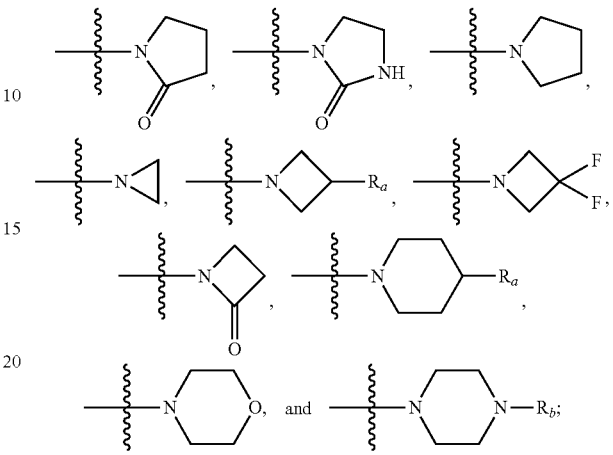

$R_a$ is H, F, $OC_{(1-3)}$alkyl, or OH;
$R_b$ is $CH_3$, or phenyl;
R⁸ is H, $CH_3$, $OCH_3$, or F;
R⁹ is H, or F;
and pharmaceutically acceptable salts thereof.

DETAILED DESCRIPTION OF THE INVENTION

The present invention comprises compounds of Formula I.

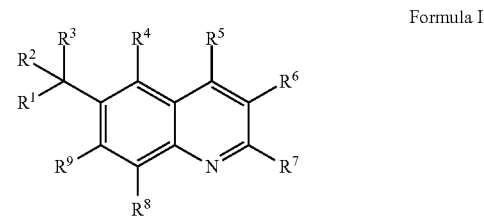

Formula I wherein:

R¹ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, $C(O)CH_3$, $C(O)NH_2$, $CH_3$, $CH_2CH_3$, $CF_3$, Cl, F, —CN, $OCH_3$, $N(CH_3)_2$, —$(CH_2)_3OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups; and wherein said azetidinyl is optionally substituted with $CO_2C(CH_3)_3$, $C(O)NH_2$, $CH_3$, $SO_2CH_3$, or $C(O)CH_3$;

R² is 1-methyl-1,2,3-triazolyl, pyridyl, pyridyl-N-oxide, 1-methyl pyrazol-4-yl, pyrimidin-5-yl, pyridazyl, pyrazin-2-yl, oxazolyl, isoxazolyl, N-acetyl-azetidin-3-yl, N-methylsulfonyl-azetidin-3-yl, N-Boc-azetidin-3-yl, N-methyl-azetidin-3-yl, N-acetamidyl-azetidin-3-yl, N-acetyl piperidinyl, 1-H-piperidinyl, N-Boc-piperidinyl, N—$C_{(1-2)}$alkyl-piperidinyl, thiazol-5-yl, 1-(3-methoxypropyl)-imidazol-5-yl, or 1-$C_{(1-2)}$alkyl imidazol-5-yl (including 1-methyl imidazol-5-yl); wherein said 1-$C_{(1-2)}$alkyl imidazol-5-yl is optionally substituted with up to two additional $CH_3$ groups, or one substituent selected from the group consisting of $SCH_3$, and Cl; and said pyridyl, and pyridyl-N-oxide are optionally substituted with up to two substituents independently selected from the group consisting of $C(O)NH_2$, —CN, $OCH_3$, $CF_3$, Cl, and $CH_3$; and said thiazol-5-yl, oxazolyl, and isoxazolyl are optionally substituted with up to two $CH_3$ groups; and said 1-methyl pyrazol-4-yl is optionally substituted with up to two additional $CH_3$ groups;

$R^3$ is H, OH, $OCH_3$, $NHCH_3$, $N(CH_3)_2$, or $NH_2$;

$R^4$ is H, or F;

$R^5$ is H, Cl, —CN, $CF_3$, $SCH_3$, $OC_{(1-3)}$alkyl, OH, $C_{(1-4)}$alkyl, $N(CH_3)OCH_3$, $NH(C_{(1-2)}$alkyl), $N(C_{(1-2)}$alkyl)$_2$, NH-cyclopropyl, $OCHF_2$, 4-hydroxy-piperidinyl, azetidin-1-yl, or fur-2-yl;

$R^6$ is —O-phenyl, —NHphenyl, —N($C_{(1-3)}$alkyl)phenyl, —N($CO_2C(CH_3)_3$)phenyl, —O-pyridyl, —NHpyridyl, —N($C_{(1-3)}$alkyl)pyridyl, or —N($CO_2C(CH_3)_3$)pyridyl wherein said phenyl portions thereof or said pyridyl portions thereof are optionally substituted with $OCF_3$, $SO_2CH_3$, $CF_3$, $CHF_2$, imidazol-1-yl, pyrazol-1-yl, 1,2,4-triazol-1-yl, $CH_3$, $OCH_3$, Cl, F, or —CN;

$R^7$ is H, Cl, —CN, $C_{(1-4)}$alkyl, $OCH_2CF_3$, $OCH_2CH_2OCH_3$, $CF_3$, $SCH_3$, $SO_2CH_3$, $OCHF_2$, $NA^1A^2$, $C(O)NHCH_3$, $N(CH_3)CH_2CH_2NA^1A^2$, $OCH_2CH_2NA^1A^2$, $OC_{(1-3)}$alkyl, $OCH_2$-(1-methyl)-imidazol-2-yl, imidazol-2-yl, fur-2-yl, pyrazol-4-yl, pyrid-3-yl, or pyrimidin-5-yl; thiophen-3-yl, 1-methyl-indazol-5-yl, 1-methyl-indazol-6-yl, phenyl, or wherein said imidazolyl or pyrazolyl can be optionally substituted with a $CH_3$ group;

$A^1$ is H or $C_{(1-4)}$alkyl (including $CH_2CH_3$);

$A^2$ is H, $C_{(1-4)}$alkyl (including $CH_2CH_3$), cyclopropyl, $C_{(1-4)}$alkyl$OC_{(1-4)}$alkyl, $C_{(1-4)}$alkyl$OH$, $C(O)C_{(1-2)}$alkyl, or $OCH_3$; or $A^1$ and $A^2$ may be taken together with their attached nitrogen to form a ring selected from the group consisting of:

$R_a$ is H, F, $OC_{(1-3)}$alkyl, or OH;

$R_b$ is $CH_3$, or phenyl;

$R^8$ is H, $CH_3$, $OCH_3$, or F;

$R^9$ is H, or F;

and pharmaceutically acceptable salts thereof.

In another embodiment of the invention:

$R^1$ is 6-trifluoromethyl pyrid-3-yl, pyrid-2-yl, 4-chlorophenyl, or 3-chlorophenyl;

$R^2$ is 1-methyl imidazol-5-yl, or pyrid-3-yl;

$R^3$ is OH;

$R^4$ is H;

$R^5$ is Cl, or —CN;

$R^6$ is —O-phenyl, or —N($CO_2C(CH_3)_3$)phenyl, wherein said —O-phenyl is optionally substituted with —CN, or Cl;

$R^7$ is Cl, $NA^1A^2$;

$A^1$ is $CH_2CH_3$;

$A^2$ is $CH_2CH_3$; or $A^1$ and $A^2$ may be taken together with their attached nitrogen to form a ring selected from the group consisting of:

and pharmaceutically acceptable salts thereof.

Another embodiment of the invention is a compound selected from the group consisting of:

-continued

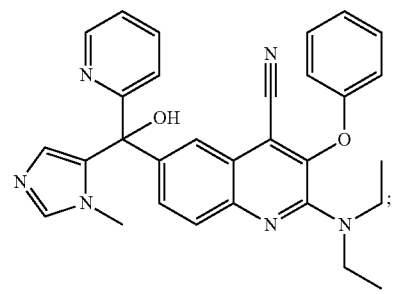

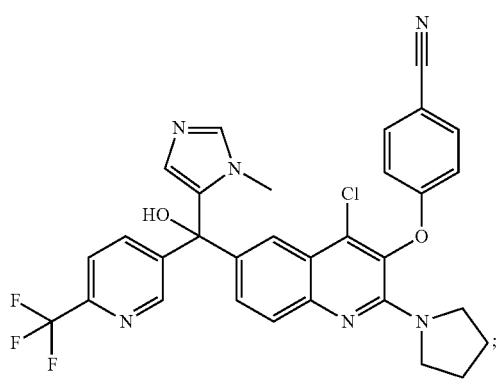

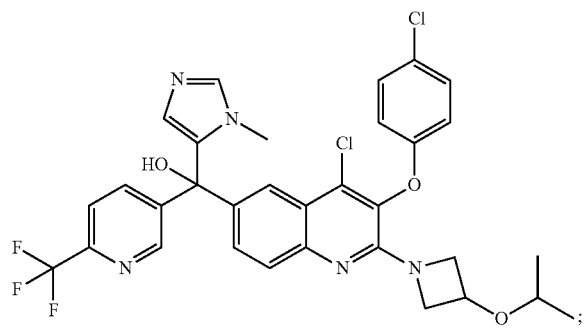

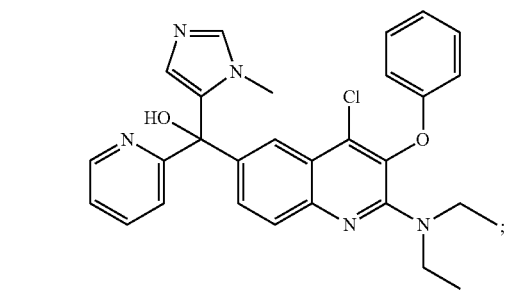

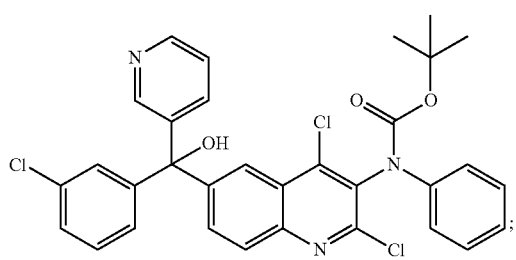

-continued

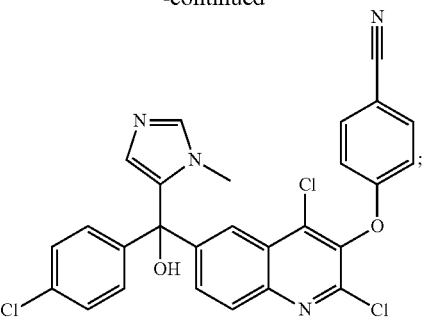

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodontitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel diseases, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The invention also relates to methods of modulating RORγt activity in a mammal by administration of an effective amount of at least one compound of Formula I.

DEFINITIONS

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment and is at risk of (or susceptible to) developing a syndrome, disorder or disease that is associated with aberrant RORγt expression or RORγt overexpression, or a patient with an inflammatory condition that accompanies syndromes, disorders or diseases associated with aberrant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-6)}$cycloalkyl, $C_{(5-8)}$cycloalkyl, decahydronaphthalenyl, and 2,3,4,5,6,7-hexahydro-1H-indenyl. Any cycloalkyl group may be optionally substituted with one $OCH_3$, one OH, or up to two fluorine atoms.

As used herein, the term "thiophenyl" is intended to describe the radical formed by removing a hydrogen atom from the molecule with the structure:

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts in vivo to the specified compound after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of Formula I may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereocenter, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Abbreviations

Herein and throughout the application, the following abbreviations may be used.

1,8-ANS 1-anilinonaphthalene-8-sulfonic acid
Å angstrom
Ac acetyl
Ar aryl
ACN acetonitrile
Boc tert-butyloxy carbonyl
bs broad singlet
Bu butyl
n-BuLi n-butyllithium
d doublet
dd doublet of doublets
dba dibenzylideneacetone
DCM dichloromethane
Dess-Martin periodinane 1,1,1-tris(acetyloxy)-1,1-dihydro-1,2-benziodoxol-3-(1H)-one
DMAP dimethylaminopyridine
DMF N,N-dimethylformamide
DMSO dimethyl sulfoxide
dppf (diphenylphosphino)ferrocene
dt doublet of triplets
Eaton's Reagent 7.7 wt % phosphorus pentoxide solution in methanesulfonic acid
EDCI N-(3-dimethylaminopropyl)-N'-ethylcarbodiimide hydrochloride
ESI electrospray ionization
Et ethyl
Et$_2$O diethyl ether
EtOAc ethyl acetate
EtOH ethyl alcohol Et₃SiCl chlorotriethylsilane
GSH glutathione
HATU O-(7-azabenzotriazol-1-yl)-N,N,N',N'-tetramethyluronium hexafluorophosphate
Hunig's base N,N-diisopropylethylamine
HPLC high pressure liquid chromatography
Hz hertz
i-PrOH isopropyl alcohol
LCMS liquid chromatography-mass spectrometry
m multiplet
M molar (moles/liter)
Me methyl
Meldrum's acid 2,2-dimethyl-1,3-dioxane-4,6-dione
MeOH methanol
MHz megahertz
min minutes
mL milliliters
MTBE methyl tertiary butyl ether
nm nanometers
NaO$^i$Pr sodium isopropoxide
NBS N-bromosuccinimide
NMR nuclear magnetic resonance
Ph phenyl
ppm parts per million
Pr propyl
q quartet
s singlet
t triplet
td triplet of doublets
TFA trifluoroacetic acid
THF tetrahydrofuran
TLC thin layer chromatography
UV ultra-violet
X-phos 2-dicyclohexylphosphino-2',4',6'-triisopropylbiphenyl General Schemes:

Compounds of Formula I in the present invention can be synthesized in accordance with the general synthetic methods known to those who are skilled in the art. The following reaction schemes are only meant to represent examples of the invention and are in no way meant to be a limit of the invention.

Scheme 1

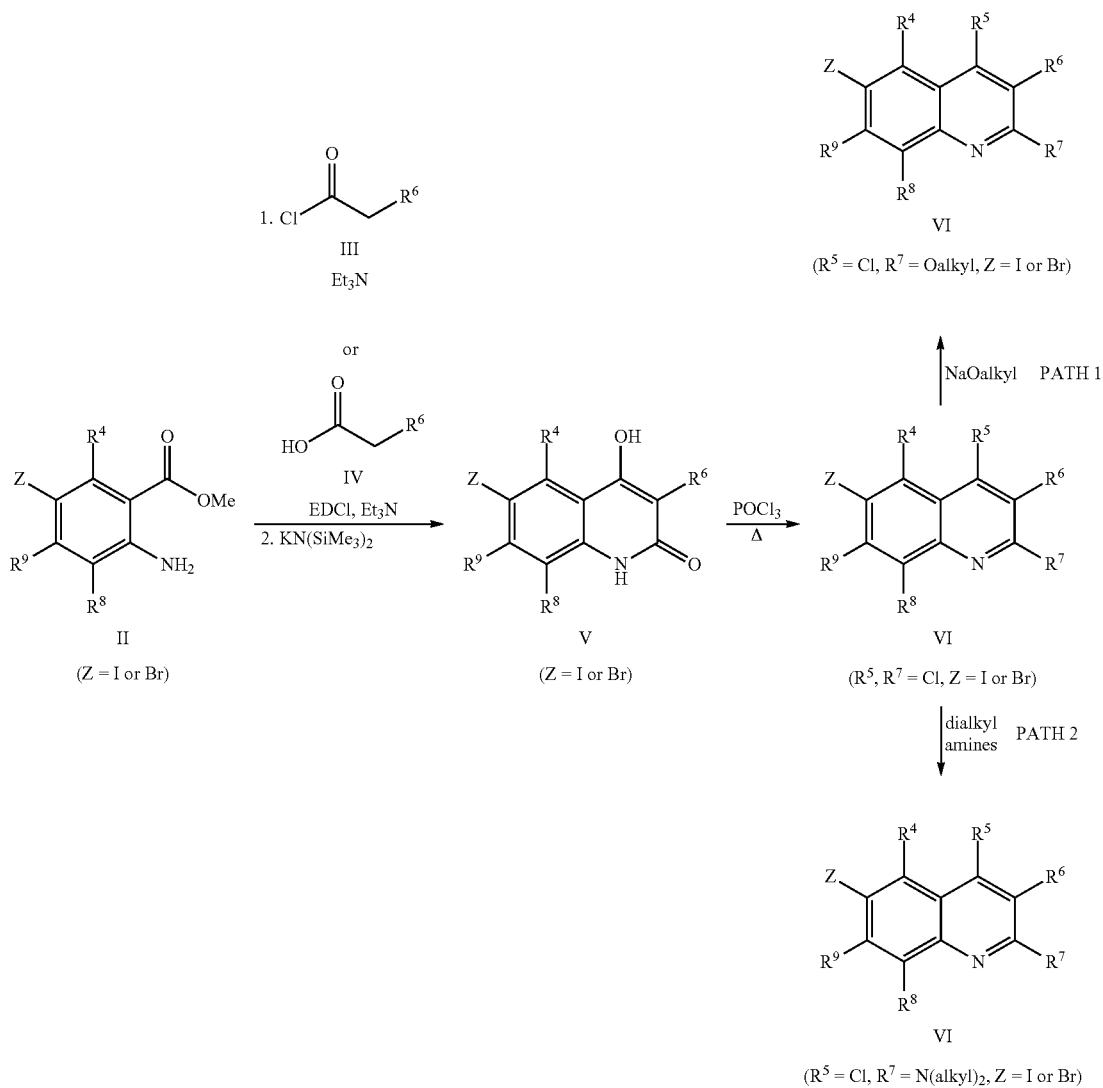

Scheme 1 describes the preparation of 6-haloquinoline intermediates of Formula VI. Methyl 2-amino-5-halobenzoates II can undergo acylation with substituted acid chlorides III ($R^6$ is substituted arylamino, heteroarylamino, aryloxy, or heteroaryloxy as described above), or can be condensed with substituted carboxylic acids IV using EDCI and a base, to form amide intermediates. The acid chlorides III can be obtained commercially or prepared from the corresponding carboxylic acids using methods known in the art. The amide intermediates can be cyclized by treatment with a base, such as potassium bis(trimethylsilyl)amide, to afford 6-halo-4-hydroxyquinolin-2(1H)-ones V. Heating hydroxyquinolin-2(1H)-ones V with phosphorus oxychloride, neat or in a solvent such as acetonitrile, yields 2,4-dichloroquinolines VI. Displacement of the 2-Cl of 2,4-dichloroquinolines VI with sodium alkoxides can be accomplished in an alcoholic solvent such as methanol, ethanol or isopropanol or at elevated temperatures in a non-polar solvent such as toluene (Alan Osborne et. al. *J. Chem. Soc. Perkin Trans.* 1 (1993) 181-184 and *J. Chem. Research* (S), 2002, 4) to provide substituted quinolines VI wherein $R^5$ is Cl and $R^7$ is Oalkyl (path 1). Additional intermediates of Formula VI where $R^7$ is $N(alkyl)_2$ can be obtained by displacement of the 2-Cl group of 2,4-dichloroquinolines VI with disubstituted amines, such as $NHMe_2$, $NHEt_2$, NHMeEt, or azetidine in a hot polar solvent, such as MeOH, EtOH, or DMF (path 2).

Scheme 2

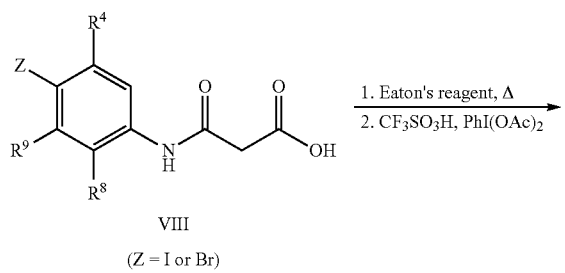

VII (Z = I or Br)

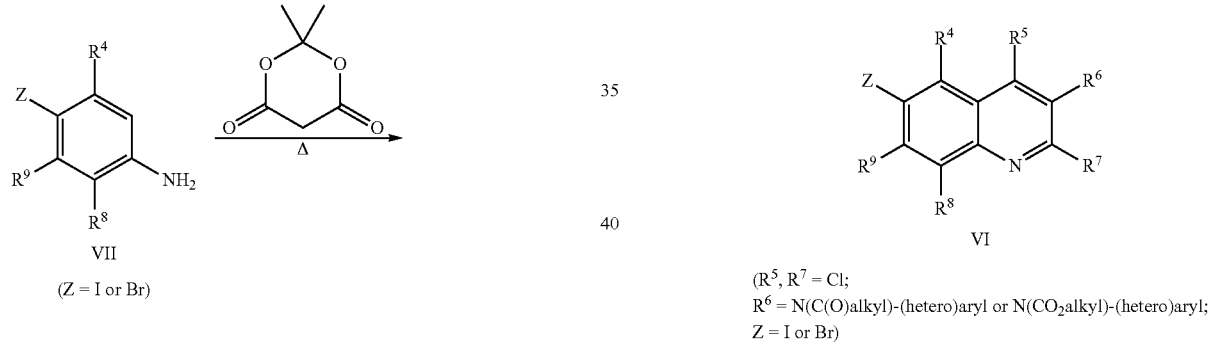

VIII (Z = I or Br)

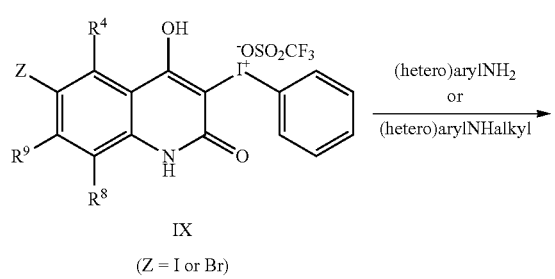

IX (Z = I or Br)

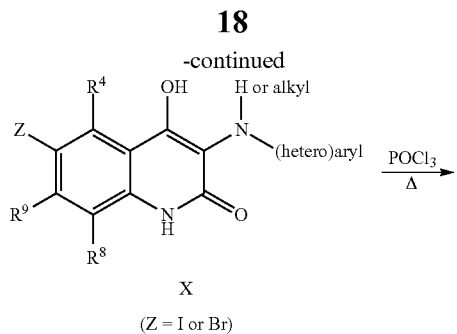

X (Z = I or Br)

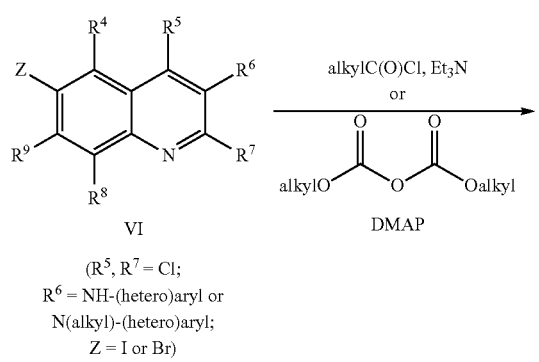

VI ($R^5$, $R^7$ = Cl;
$R^6$ = NH-(hetero)aryl or N(alkyl)-(hetero)aryl;
Z = I or Br)

VI ($R^5$, $R^7$ = Cl;
$R^6$ = N(C(O)alkyl)-(hetero)aryl or N($CO_2$alkyl)-(hetero)aryl;
Z = I or Br)

An alternative route to 6-haloquinolines VI where $R^6$ is substituted arylamino or heteroarylamino is shown in Scheme 2. 4-Haloanilines VII can be heated with 2,2-dimethyl-1,3-dioxan-4,6-dione (Meldrum's acid) to form 3-((4-halophenyl)amino)-3-oxopropanoic acids VIII. Cyclization of VIII in Eaton's reagent at elevated temperature then affords 4-hydroxyquinolinone intermediates (Synth. Commun. 2010, 40, 732), which can be treated with (diacetoxyiodo)benzene and trifluoromethanesulfonic acid to yield 4-hydroxyquinolinone phenyliodoniumtrifluoromethane sulfonates IX (Org. React. 2001, 57, 327). Reaction of these intermediates with arylamines or heteroarylamines yields substituted 3-amino-4-hydroxyquinolinones X (Monatsh. Chem. 1984, 115 (2), 231), which may be heated in phosphorus oxychloride to afford 2,4-dichloroquinolines VI. In cases where $R^6$ is a secondary amine, these intermediates may be further functionalized to form amides by reaction with an acid chloride and a tertiary amine base, or to form carbamates by reaction with a dialkyl dicarbonate, such as di-tert-butyl dicarbonate, and DMAP in a polar solvent such as THF or DMF.

Scheme 3

PATH 1

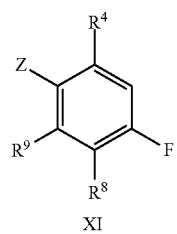

XI
(Z = I or Br)

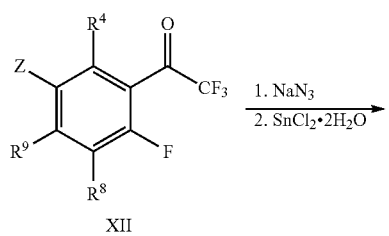

XII

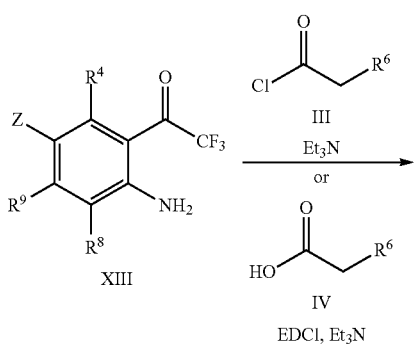

XIII

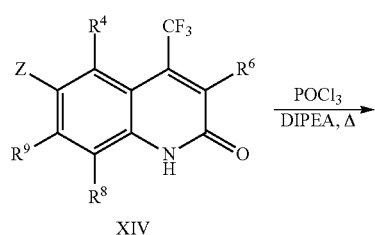

XIV

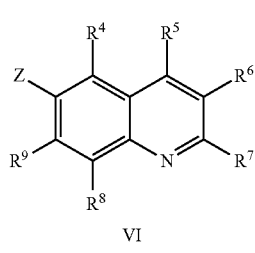

VI
($R^5$ = $CF_3$, $R^7$ = Cl, Z = I or Br)

PATH 2

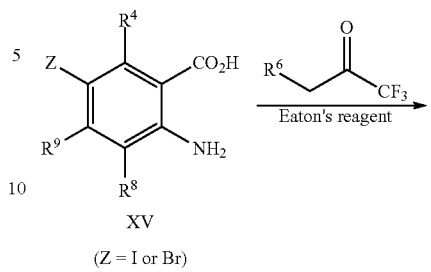

XV
(Z = I or Br)

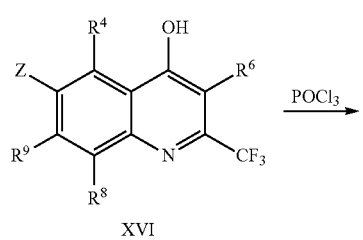

XVI

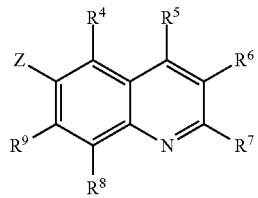

VI
($R^5$ = Cl, $R^7$ = $CF_3$, Z = I or Br)

Scheme 3 describes the synthesis of 2- and 4-trifluoromethylquinolines VI. Treatment of 1-halo-4-fluorobenzenes XI with lithium diisopropylamide at −78° C. followed by addition of ethyl trifluoroacetate gives 2-fluorophenyl-2,2,2-trifluoroethanones XII. Displacement of the 2-fluoro substituent in XII with sodium azide followed by reduction of the azide intermediates, for example with tin (II) chloride dihydrate, yields anilines XIII. Acylation of anilines XIII with acid chlorides III or with carboxylic acids IV in the presence of a coupling agent such as EDCI and base, such as triethylamine or potassium tert-butoxide, leads directly to cyclized quinolin-2(1H)-ones XIV. Heating 4-(trifluoromethyl)quinolin-2(1H)-ones XIV with phosphorus oxychloride in the presence of diisopropylethylamine yields 6-haloquinolines VI wherein $R^5$ is $CF_3$ and $R^7$ is Cl (path 1). 4-Chloro-2-(trifluoromethyl)quinolines can be prepared starting from 2-aminobenzoic acids XV (path 2). Cyclization of XV with substituted 1,1,1-trifluoropropan-2-ones in Eaton's reagent at elevated temperatures yields 4-hydroxy-2-(trifluoromethyl)quinolines XVI, which upon heating in phosphorus oxychloride yields 6-haloquinolines VI wherein $R^5$ is Cl and $R^7$ is $CF_3$.

Scheme 4
PATH 1
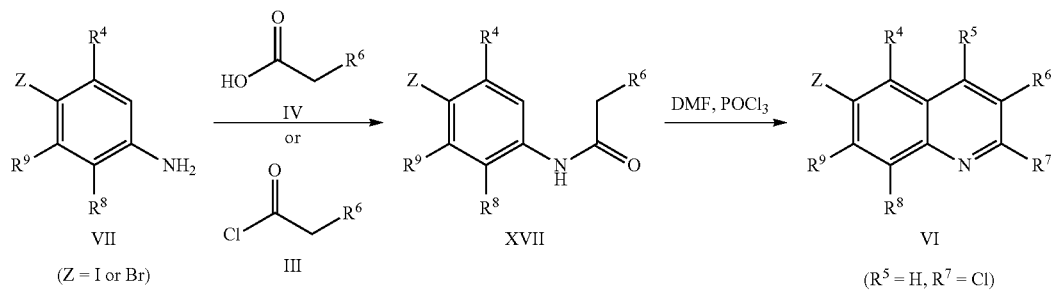
PATH 2
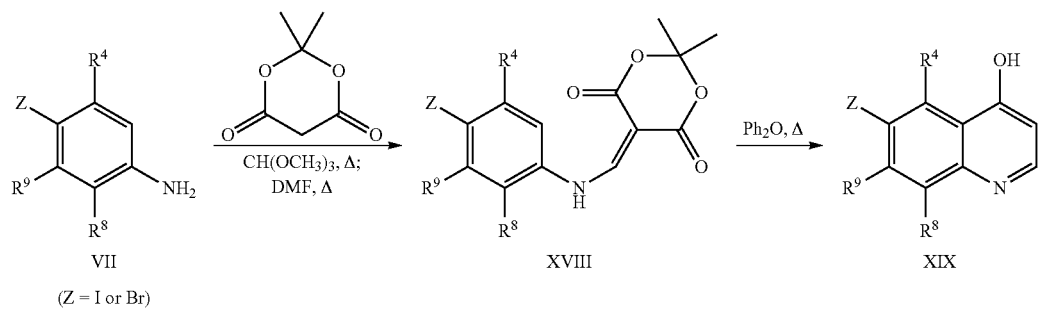
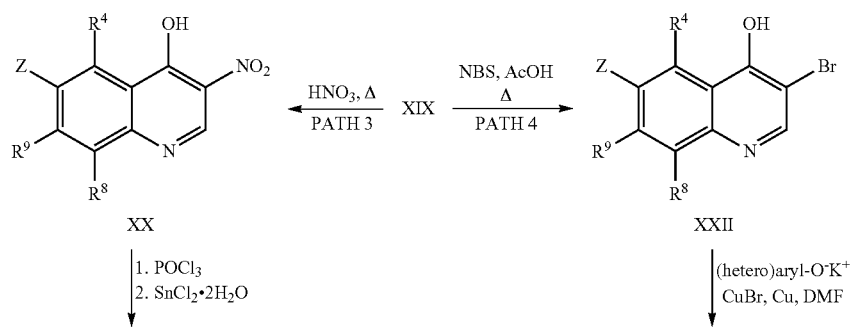
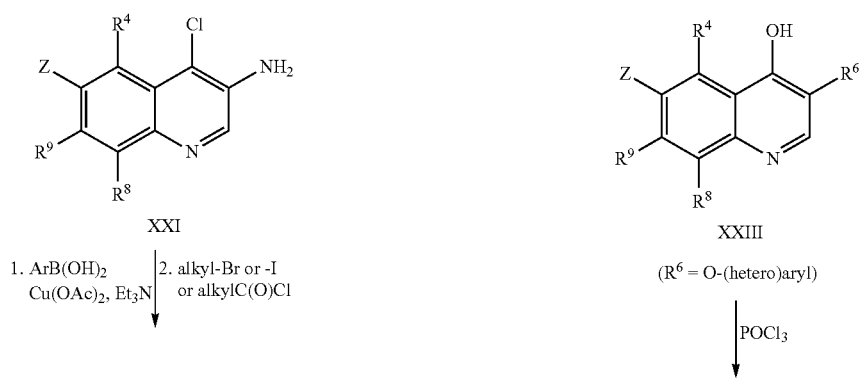

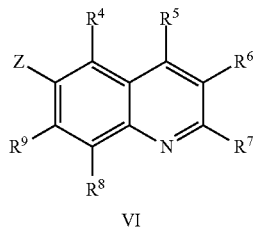

VI ($R^5$ = Cl, $R^7$ = H; $R^6$ = N(alkyl)-(hetero)aryl or N(C(O)alkyl)-(hetero)aryl; Z = I or Br)

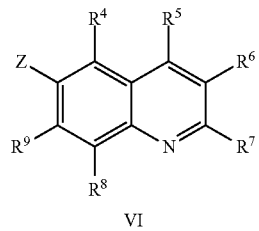

VI ($R^5$ = Cl, $R^7$ = H; $R^6$ = O-(hetero)aryl; Z = I or Br)

Scheme 4 illustrates methods for the preparation of 6-haloquinoline intermediates VI in which either $R^5$ or $R^7$ is hydrogen. Amides XVII, formed by acylation of anilines VII as previously described above, can be cyclized to quinolines VI wherein $R^5$ is H and $R^7$ is Cl by formylation using Vilsmeier-Haack conditions ($POCl_3$/DMF) followed by heating to promote ring cylization (path 1). 6-Haloquinolines VI where $R^5$ is Cl and $R^7$ is H can be prepared by the methods shown in paths 2, 3 and 4. 4-Haloanilines VII can be reacted with in situ generated methoxymethylene Meldrum's acid to form enamines XVIII which can cyclize by heating in the range of 250-300° C. in a non-polar high-boiling solvent such as diphenyl ether, to provide 4-hydroxyquinolines XIX (Madrid, P. B. et al., Bioorg. Med. Chem. Lett., 2005, 15, 1015). 4-Hydroxyquinolines XIX may be nitrated at the 3-position by heating with nitric acid in an acidic solvent, such as propionic acid, to provide 3-nitro-4-hydroxyquinolines XX (path 3). Heating these intermediates with $POCl_3$ and reduction of the nitro group, for instance using tin(II) chloride dihydrate, provides 3-amino-4-chloroquinolines XXI. N-arylation or N-heteroarylation can be accomplished using aryl or heteroaryl boronic acids and a copper salt, such as $Cu(OAc)_2$, in the presence of a tertiary amine base. The resulting secondary amines can be further elaborated to 6-haloquinolines of Formula VI where is $R^5$ is Cl, $R^6$ is substituted arylamino or heteroarylamino, and $R^7$ is H by N-alkylation or acylation with an alkyl halide or acid chloride, respectively, in the presence of a base. Alternatively, 4-hydroxyquinolines XIX may be brominated at the 3-position by heating with N-bromosuccinamide in acetic acid to furnish 3-bromo-4-hydroxyquinolines XXII (path 4). Displacement of the 3-bromo substituent can be accomplished by heating with an aryl or heteroaryl potassium phenoxide salt in the presence of copper powder and copper (I) bromide in a polar solvent, such as DMF, as described in Collini, M. D. et al., US 20050131014. The resulting 4-hydroxyquinolines XXIII can be heated in $POCl_3$ to provide 6-haloquinolines VI where $R^5$ is Cl, $R^6$ is aryloxy or heteroaryloxy, and $R^7$ is H.

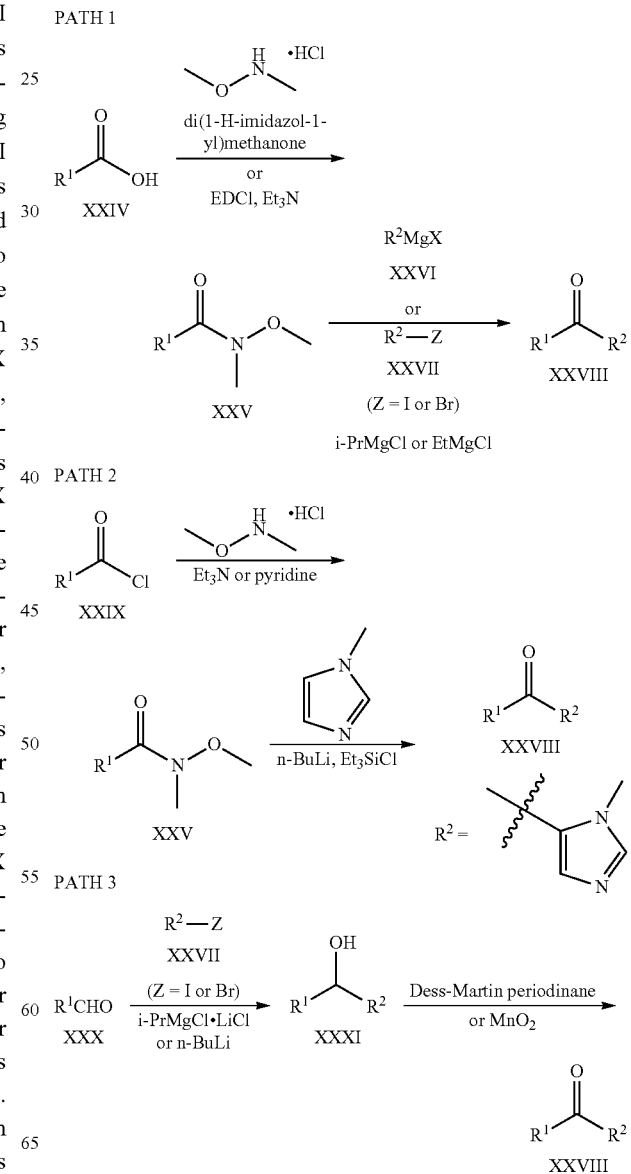

Scheme 5

PATH 4

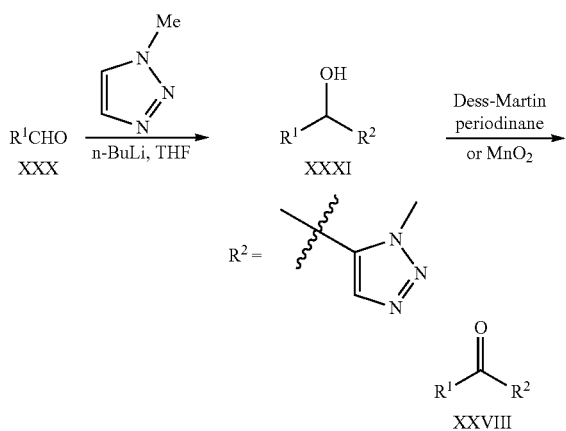

PATH 5

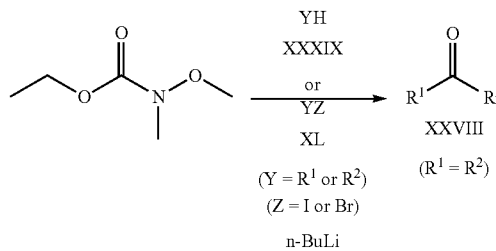

PATH 6

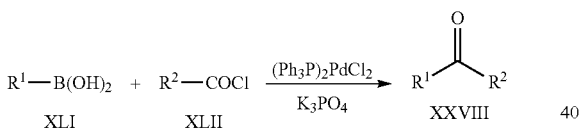

Scheme 5 illustrates synthetic routes (path 1 to 6) to ketones of Formula XXVIII. In path 1, Weinreb amide XXV can be prepared from acids XXIV by reacting with N,O-dimethylhydroxylamine hydrochloride and 1,1-carbonyldiimidazole or with N,O-dimethylhydroxylamine hydrochloride in the presence of a base such as triethylamine or Hunig's base and a coupling reagent such as EDCI. The amides XXV can be further treated with Grignard reagents such as $R^2MgX$ (X is Br or Cl) that can be obtained commercially or preformed by treatment of $R^2Z$ with organometallic reagents such as i-PrMgCl or EtMgCl in THF. Alternatively, Weinreb amides XXV can be obtained from acyl chlorides XXIX, which can be obtained commercially or prepared from the corresponding carboxylic acids using methods known in the art, and N,O-dimethylhydroxylamine hydrochloride by using triethylamine or pyridine as a base. 1-Methyl-1H-imidazole can be treated with one equivalent of n-BuLi and one equivalent of chlorotriethylsilane at −78° C. followed by an additional equivalent of n-BuLi, to which the Weinreb amides XXV can be added to yield ketones XXVIII wherein $R^2$ is imidazolyl (path 2).

In path 3, halogen-metal exchange of bromides or iodides XXVII with i-PrMgCl.LiCl or n-BuLi, followed by addition of aldehydes XXX affords alcohols XXXI. Oxidation of XXXI with Dess-Martin periodinane or $MnO_2$ can provide ketones XXVIII. In path 4, ketones XXVIII, where $R^2$ is triazolyl, can be prepared by treatment of 1-methyl-1H-1,2,3-triazole with n-BuLi followed by reaction with aldehydes XXX to yield alcohols XXXI, which could undergo oxidation with Dess-Martin periodinane or $MnO_2$. Path 5 exemplifies the preparation of symmetrical ketones XXVIII, wherein $R^1$ and $R^2$ are the same. As illustrated, an aryl or heteroaryl group containing an acidic proton XXXIX (Y=$R^1$ or $R^2$) can be deprotonated in the presence of a strong base such as n-BuLi once solubilized in a preferred solvent such as tetrahydrofuran at temperatures between 0 and −78° C. then added in excess to ethyl methoxy(methyl)carbamate to provide aryl ketones XXVIII wherein $R^1$ and $R^2$ are the same. Aryl or heteroaryl bromide or iodide XL can also be lithiated through a lithium/halogen exchange with n-BuLi before adding in excess to ethyl methoxy(methyl)carbamate as previously described to provide symmetrical ketones XXVIII. Path 6, which employs palladium catalyzed cross-coupling of aryl-boronic acids XLI with acid chlorides XLII using $K_3PO_4$ as a base and $(Ph_3P)_2PdCl_2$ as a catalyst in a high boiling nonpolar solvent such as toluene, can also be used to generate ketones XXVIII.

Scheme 6

PATH 1

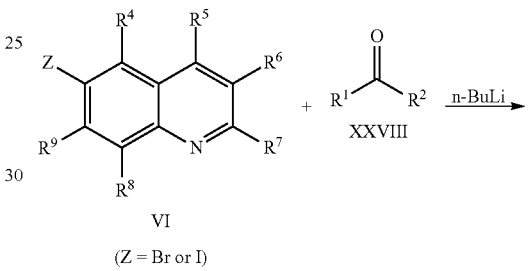

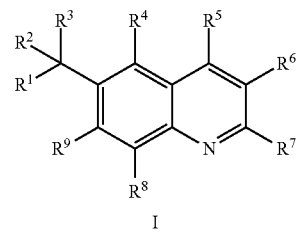

PATH 2

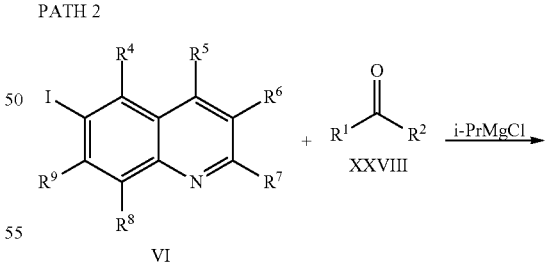

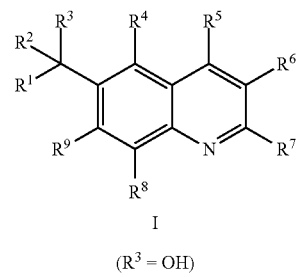

Scheme 6 illustrates synthetic routes leading to compounds of Formula I (paths 1 and 2). As illustrated in path 1, a mixture of the 6-haloquinolines VI in an appropriate solvent such as THF can be either premixed with the aryl ketones XXVIII at −78° C. followed by addition of n-BuLi or the 6-haloquinolines VI can be pretreated with n-BuLi at −78° C. prior to the addition of the aryl ketones XXVIII to afford the tertiary alcohols of Formula I, wherein $R^3$ is OH. In path 2, 6-iodoquinolines VI can be treated with i-PrMgCl followed by addition of ketones XXVIII to yield compounds of Formula I wherein $R^3$ is OH.

oxidized to ketones XXXIII with Dess-Martin periodinane or $MnO_2$. Alternatively, ketones XXXIII may be prepared by treatment of 6-haloquinolines VI with n-BuLi at −78° C. followed by quenching with DMF affording quinoline carboxaldehydes XXXIV. Ketones XXXIII can be obtained in a two-step process by addition of aldehydes XXXIV to a reaction mixture of aryl iodides XXXV and i-PrMgCl.LiCl followed by oxidation with $MnO_2$ (path 2). Halogen-metal exchange of aryl halides (iodide or bromide) XXVII with an

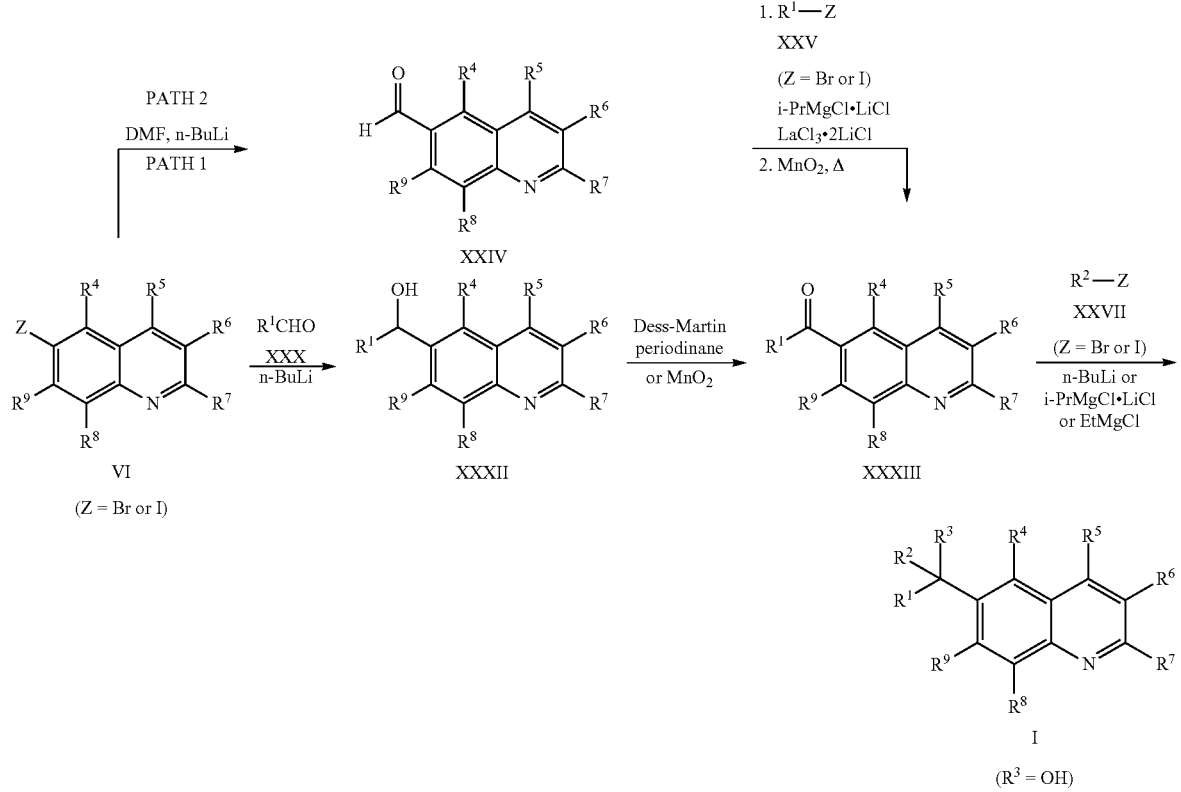

An alternative route to compounds of Formula I is shown in Scheme 7. In path 1, treatment of 6-haloquinolines VI with n-BuLi at −78° C. followed by addition of aldehydes XXX provides secondary alcohol quinolines XXXII, which can be organometallic reagent, such as n-BuLi, i-PrMgCl.LiCl, or EtMgCl, at an appropriate temperature, such as −78° C. or 0° C., followed by reaction with ketones XXXIII may afford tertiary alcohol quinolines of Formula I.

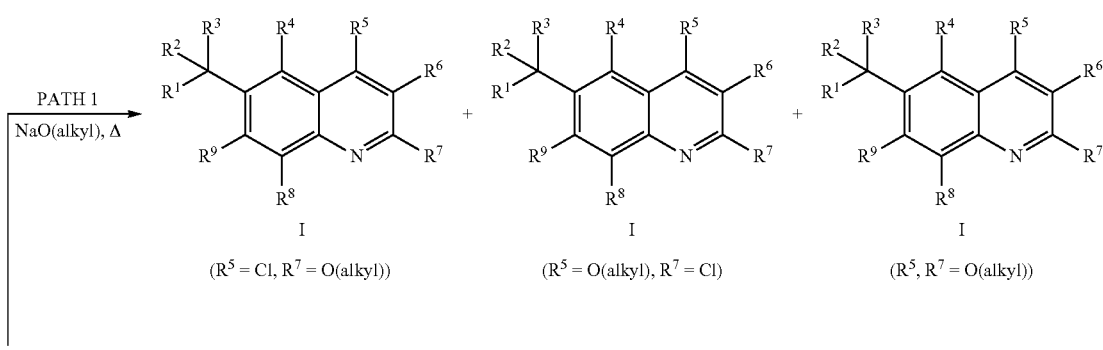

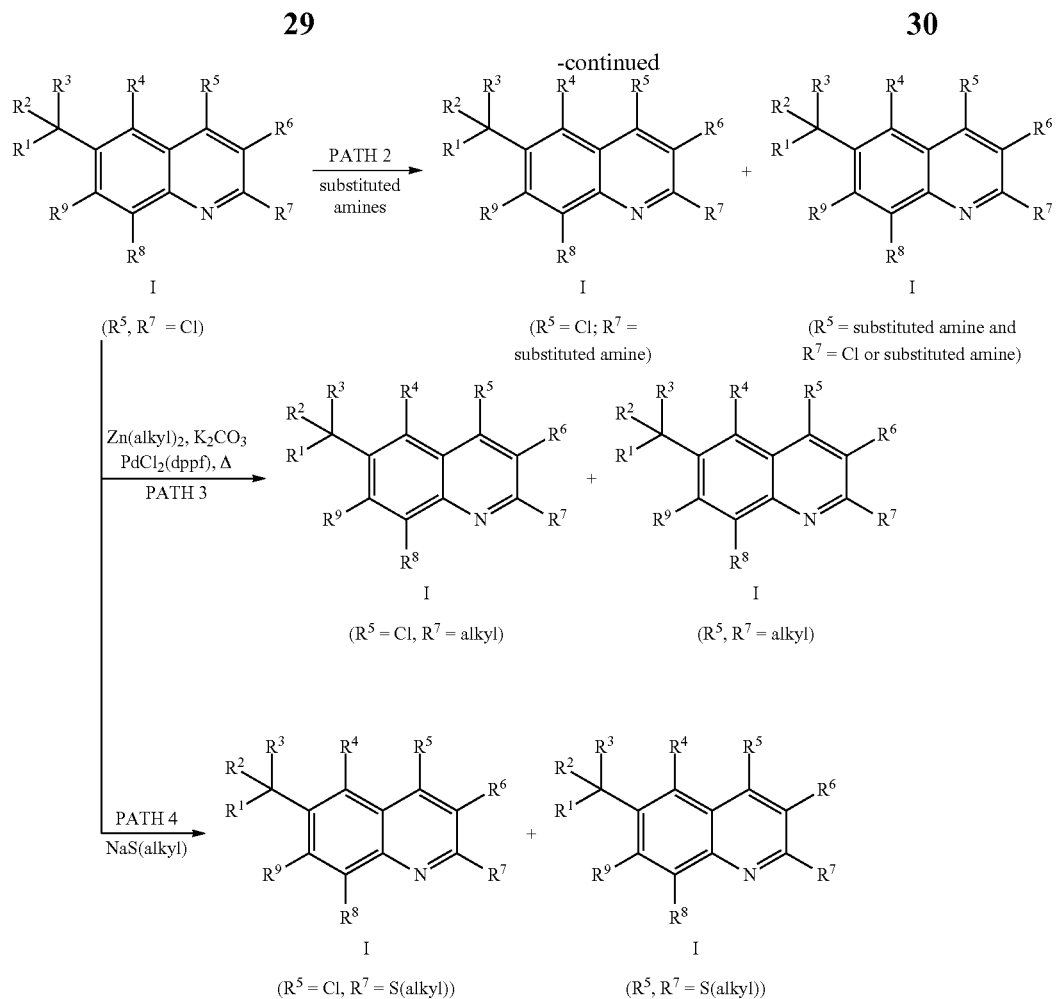

Scheme 8 illustrates methods used to synthesize compounds of Formula I wherein either the chlorine at $R^7$ or at both $R^5$ and $R^7$ positions are replaced with nitrogen, oxygen, sulfur or alkyl groups. In paths 1 and 4, nucleophilic displacement of 2,4-dichloroquinolines I ($R^5$ and $R^7$ are Cl) with NaO(alkyl) or NaS(alkyl), such as NaOMe, NaSMe, NaOEt, or NaO$^i$Pr, in an appropriate solvent, such as MeOH, EtOH, i-PrOH or DMF at elevated temperatures or with substituted hydroxy reagents such as 2-methoxyethanol in the presence of a base like sodium hydride in a non-polar solvent such as toluene provides compounds of Formula I wherein $R^5$ is Cl and $R^7$ is O(alkyl), O(CH$_2$)$_2$OCH$_3$ or S(alkyl) and compounds of Formula I wherein $R^5$ and $R^7$ are O(alkyl) or S(alkyl). Likewise, nucleophilic displacement of 2,4-dichloroquinolines I ($R^5$ and $R^7$ are Cl) with primary or secondary alkyl amines, heterocyclic amines, or N,O-dimethylhydroxylamine in polar solvents such as MeOH, EtOH, Et$_2$NCHO, or DMF provides quinolines of Formula I (path 2) wherein $R^5$ is NH(alkyl), N(alkyl)$_2$, N(CH$_3$)OCH$_3$, or Cl, and $R^7$ is NH(alkyl), N(alkyl)$_2$, N(CH$_3$)OCH$_3$, NA$^1$A$^2$, NHC$_{(2-3)}$alkylNA$^1$A$^2$ or N(CH$_3$)C$_{(2-4)}$alkylNA$^1$A$^2$, wherein A$^1$ and A$^2$ are as defined above. Introduction of cyclic amides can be accomplished using Buchwald palladium catalyzed coupling conditions to provide compounds of Formula I, wherein $R^7$ are rings such as azetidin-2-ones or pyrrolidin-2-ones. Replacement of chlorine at positions 2- and 4- of quinolines I ($R^5$ and $R^7$ are Cl) with alkyl groups could be carried out using Zn(alkyl)$_2$ in the presence of K$_2$CO$_3$ and a palladium catalyst, such as PdCl$_2$(dppf), to afford 2-alkyl and 2,4-dialkylquinolines I (path 3).

Scheme 9

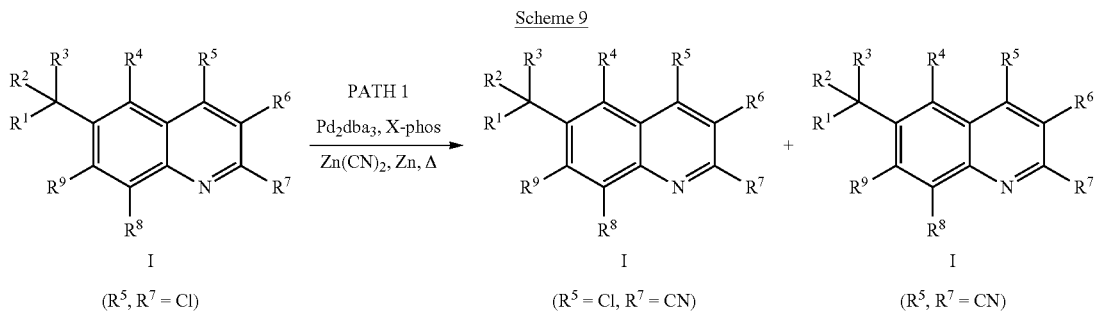

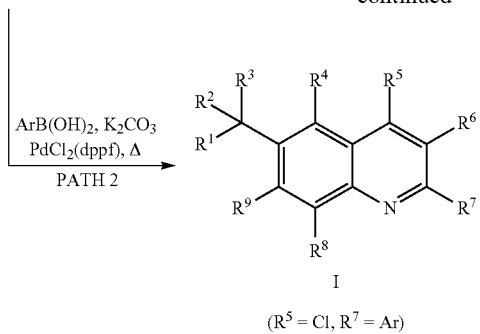

(R⁵ = Cl, R⁷ = Ar)

Synthetic routes to compounds of Formula I, wherein R⁵ is Cl or CN, and R⁷ is CN or aryl, are illustrated in Scheme 9. In path 1, cyanation of the 2,4-dichloroquinolines I with Zn(CN)₂ in the presence of Zn (dust, <10 μm), a palladium catalyst, such as Pd₂dba₃, and a ligand, such as dppf or X-phos, at high temperatures can provide 2-CN and 2,4-diCN quinolines I. The 2,4-dichloroquinolines I can also undergo Suzuki reactions with ArB(OH)₂ or ArB(OR)₂ and a palladium catalyst, such as PdCl₂(dppf), yielding compounds of Formula I wherein R⁷ is phenyl, substituted phenyl and five or six-membered ring heteroaryls such as furan, pyridine, pyridazine, pyrazine, pyrimidine, pyrrole, pyrazole, or imidazole (path 2).

As illustrated in Scheme 10, compounds of Formula I prepared in Schemes 8 and 9 wherein R⁵ is a chlorine and R⁷ is not a chlorine can be further substituted by treatment with alkylboronic acids or esters under Suzuki reaction conditions (path 1), with sodium alkoxides (path 2), or with zinc cyanide (path 3) using conditions previously described to provide compounds of Formula I wherein R⁵ is alkyl, O(alkyl) or CN and R⁷ is as described above.

Scheme 10

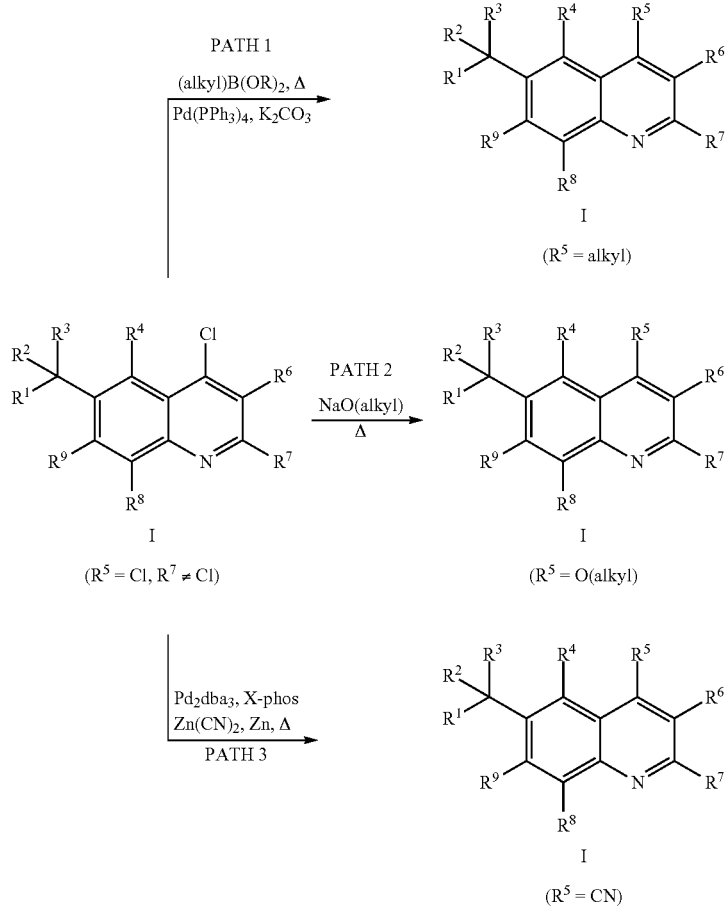

Scheme 11

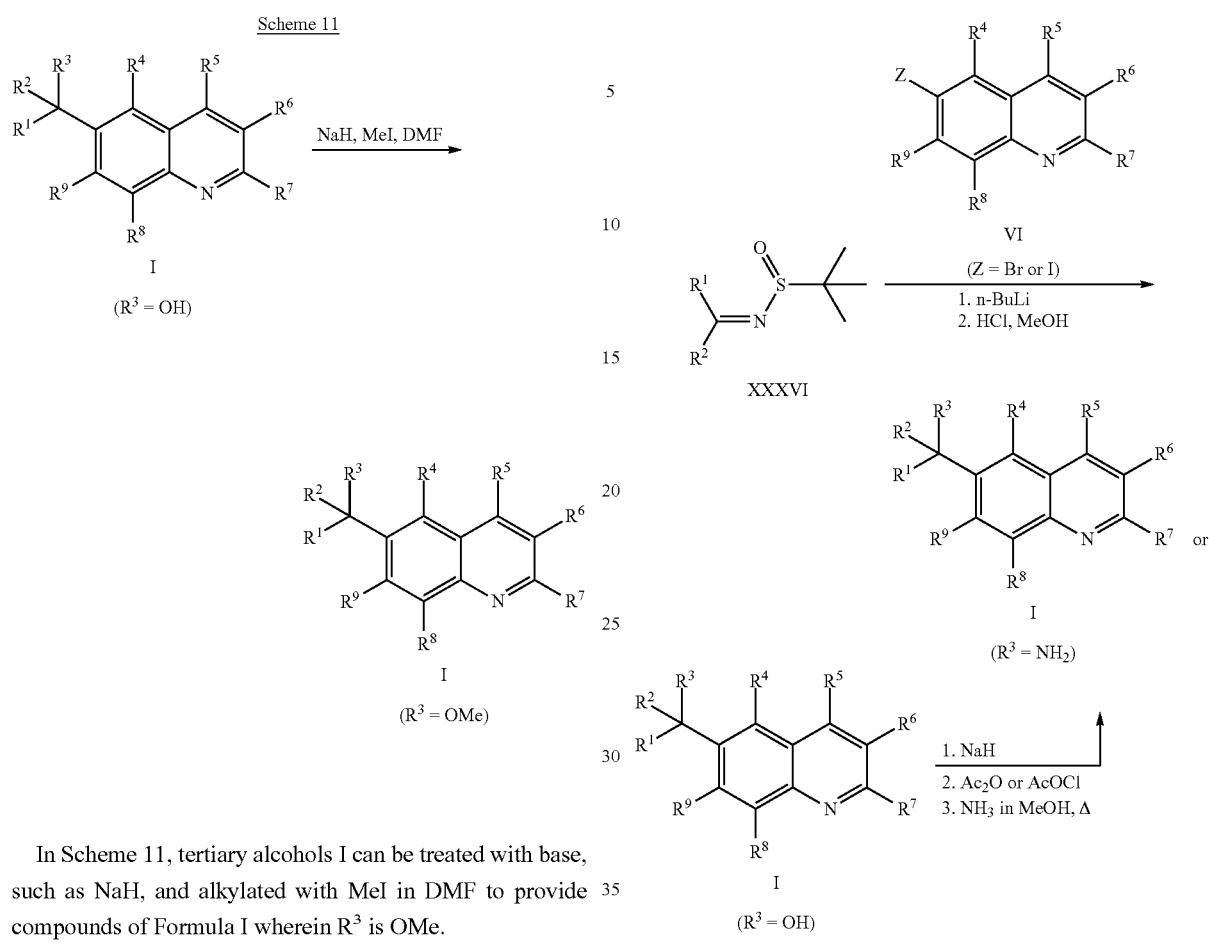

In Scheme 11, tertiary alcohols I can be treated with base, such as NaH, and alkylated with MeI in DMF to provide compounds of Formula I wherein $R^3$ is OMe.

Synthetic routes to compounds of Formula I, wherein $R^3$ is $NH_2$, are illustrated in Scheme 12. Ketimines XXXVI may be prepared by $Ti(OEt)_4$ mediated condensation of ketones XXVIII with 2-methylpropane-2-sulfinamide in refluxing THF. Addition of n-BuLi to the reaction mixture of ketimines XXXVI and 6-haloquinolines VI at −78° C. followed by cleavage of the tert-butanesulfinyl group with HCl in MeOH liberates amines I. Alternatively, compounds of Formula I, wherein $R^3$ is OH can be treated with sodium hydride followed by addition of acetic anhydride or acetyl chloride and stirred at room temperature over a 24 to 72 hour period to provide the intermediate acetate wherein $R^3$ is OAc. The acetate can then be combined with a solution of ammonia in methanol and heated at temperatures between 60 and 85° C. to provide compounds of Formula I, wherein $R^3$ is $NH_2$.

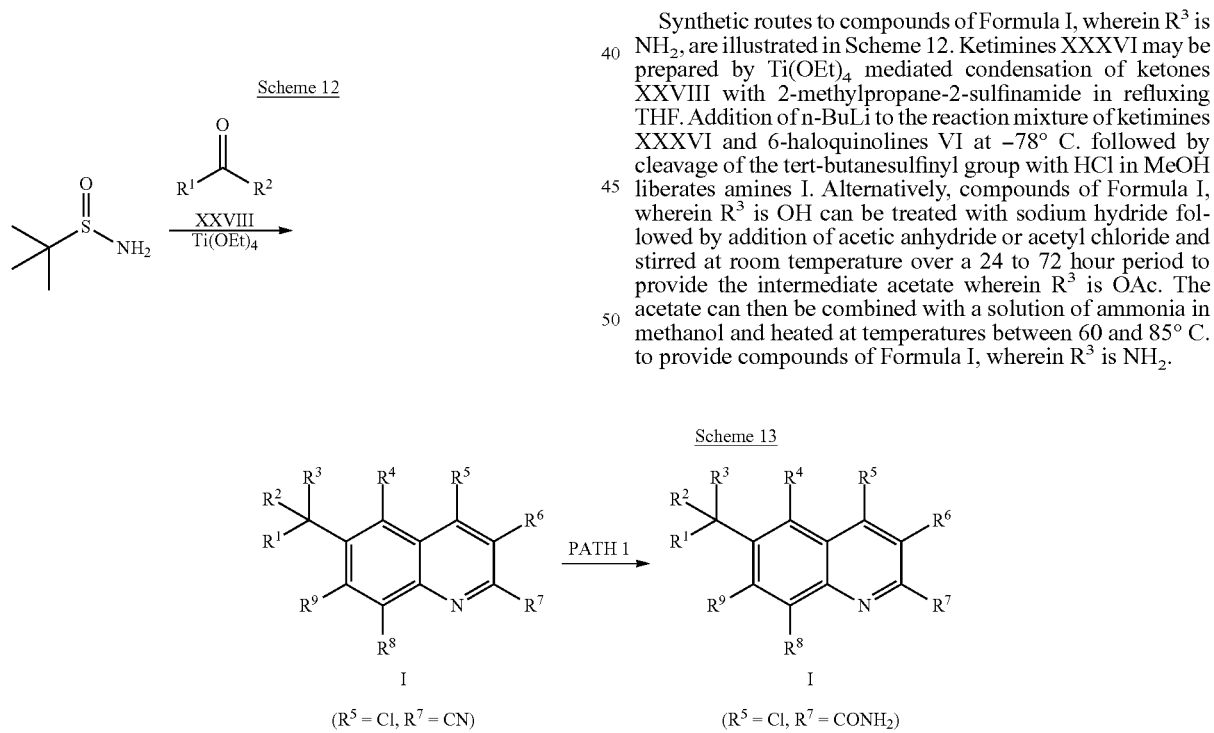

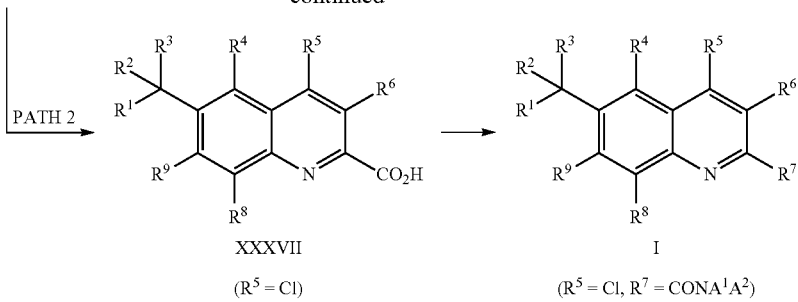

As shown in Scheme 13, the quinolines of Formula I wherein $R^7$ is —CN can be hydrolyzed as described in US20080188521 by treatment with sodium carbonate and hydrogen peroxide to provide compounds of Formula I wherein $R^7$ is $CONH_2$ (path 1) or can be treated with a strong acid like HCl to convert —CN to a carboxylic acid (path 2). Once formed the acid XXXVII can be further coupled to substituted amines using appropriate coupling reagents such as EDCI or HATU in the presence of a base such as triethylamine or Hunig's base to provide compounds of Formula I wherein $R^7$ is $CONA^1A^2$.

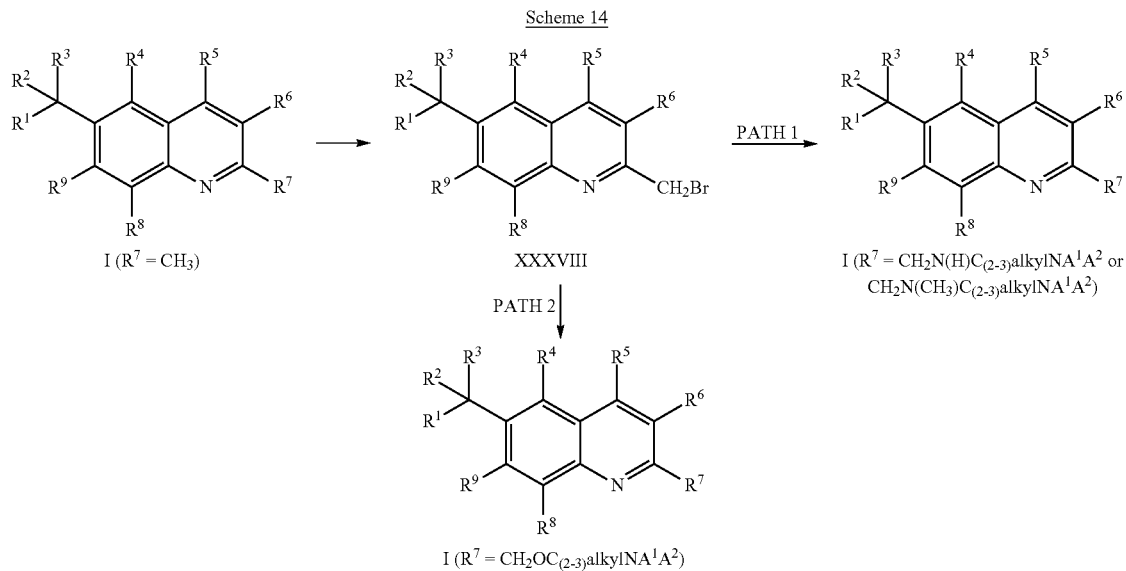

Synthesis of compounds of Formula I, wherein $R^7$ is an aminoalkylaminomethylene or an aminoalkoxymethylene can be prepared from 2-methylquinolines as shown in Scheme 14. Bromination of 2-methylquinolines of Formula I can be accomplished with N-bromosuccinamide in acetic acid at elevated temperatures as described in WO2010151740, to provide the methylbromide intermediates XXXVIII. Nucleophilic displacement of the bromide under basic conditions using procedures known in the art could afford compounds of Formula I wherein $R^7$ is —$CH_2$(H)$C_{(2-3)}$alkylN$A^1A^2$ or —$CH_2N(CH_3)C_{(2-3)}$alkylN$A^1A^2$ (path 1) or $CH_2OC_{(2-3)}$alkylN$A^1A^2$ (path 2) and $A^1$ and $A^2$ are defined above.

Compounds of Formula I wherein $R^1$, $R^2$ or $R^6$ are pyridyl can be treated with m-chloroperbenzoic acid in a chlorinated solvent at ambient to 40° C. to form the pyridyl-N-oxides of Formula I.

-continued

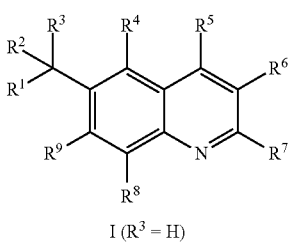

I ($R^3$ = H)

As shown in Scheme 15, compounds of the Formula I wherein $R^3$ is H can be prepared by treating compounds of Formula I wherein $R^3$ is OH with an acid such as trifluoracetic acid in a solvent such as dichloromethane at room temperature or with heating (WO2009091735).

EXAMPLES

Compounds of the present invention can be prepared by methods known to those who are skilled in the art. The following examples are only meant to represent examples of the invention and are in no way meant to be a limit of the invention.

Intermediate 1

Step a

4-Chloro-N-methoxy-N-methylbenzamide

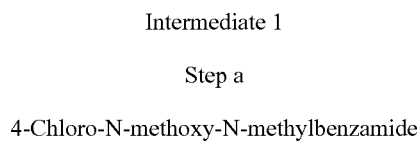

Pyridine (27.6 mL, 343 mmol) was added to N,O-dimethylhydroxylamine hydrochloride (16.7 g, 172 mmol) in DCM (400 mL). 4-Chlorobenzoyl chloride (20 mL, 156 mmol) was then added and the mixture was stirred at room temperature for 3 days. Solids were removed by vacuum filtration and washed with DCM. The filtrate was washed with 1 N aqueous HCl followed by water. The organic phase was dried ($Na_2SO_4$), filtered, and concentrated, affording the crude title compound as a colorless liquid which was used without purification in the next step.

Intermediate 1

Step b (4-Chlorophenyl)(1-methyl-1H-imidazol-5-yl)methanone

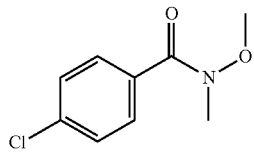

Ethyl magnesium bromide (3.0 M in diethyl ether, 21.5 mL, 64.4 mmol) was added via syringe over a few minutes to a clear colorless solution of 5-bromo-1-methyl-1H-imidazole (10.4 g, 64.4 mmol) in THF (100 mL) under a nitrogen atmosphere in an ice bath. A white precipitate formed during the addition. The mixture was removed from the ice bath and was stirred for 20 min, then was again cooled in an ice bath before addition of 4-chloro-N-methoxy-N-methylbenzamide (10.7 g, 53.6 mmol, Intermediate 1: step a). The resulting white suspension was stirred overnight at room temperature. The reaction was quenched by addition of saturated aqueous $NH_4Cl$ and diluted with water. The mixture was partially concentrated to remove THF and was diluted with DCM. The mixture was acidified to pH 1 with 1 N aqueous HCl, then neutralized with saturated aqueous $NaHCO_3$. The phases were separated and the aqueous phase was further extracted with DCM. The organic extracts were washed with water, then were dried ($Na_2SO_4$), filtered, and concentrated, affording a white solid. The crude product was triturated with a mixture of EtOAc:heptanes (1:1, 150 mL). The precipitated solid was collected by vacuum filtration and washed with heptanes to afford the title compound.

Intermediate 2

Step a 2-(4-Cyanophenoxy)acetyl chloride

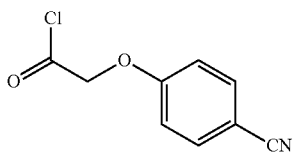 [SMILES: N#Cc1ccc(OCC(=O)Cl)cc1]

To a suspension of commercially available 2-(4-cyanophenoxy)acetic acid (4.0 g, 22.6 mmol) in dichloromethane (80 mL) was added oxalyl chloride (2.17 mL, 24.8 mmol). To this mixture was added N,N-dimethylformamide (30 μL) dropwise and the mixture was stirred for 2 hours during which cessation of evolution of gas was observed. The resulting solution was diluted with dichloromethane (50 mL) and the solvent was removed under reduced pressure to provide the title compound as an oil which became a solid upon storing in the refrigerator.

Intermediate 2

Step b

Methyl 5-bromo-2-(2-(4-cyanophenoxy)acetamido)benzoate

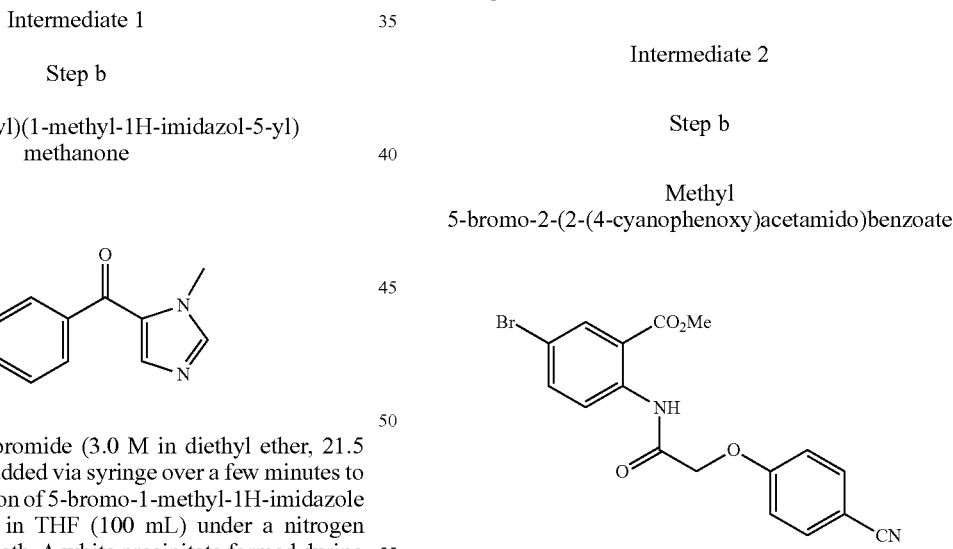

To a solution of methyl 2-amino-5-bromobenzoate (4.0 g, 17.39 mmol) in dichloromethane (60 mL) was added 2-(4-cyanophenoxy)acetyl chloride (3.74 g, 19.13 mmol, Intermediate 2: step a) to form a thick suspension. An additional 30 mL of dichloromethane was added. The reaction was then cooled to 0° C. and triethylamine (5.32 mL, 38.25 mmol) was added dropwise. The cold bath was removed and the reaction was stirred at room temperature for 2 hours, then filtered to give the title compound as a white solid. The filtrate was washed with water, followed by saturated aqueous $NH_4Cl$ solution. The organic layer was dried ($MgSO_4$), filtered, con-

Intermediate 2

Step c 4-((6-Bromo-4-hydroxy-2-oxo-1,2-dihydroquinolin-3-yl)oxy)benzonitrile

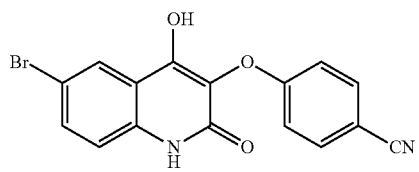 [SMILES: N#Cc1ccc(Oc2c(O)c3cc(Br)ccc3[nH]c2=O)cc1]

To a suspension of methyl 5-bromo-2-(2-(4-cyanophenoxy)acetamido)benzoate (0.240 g, 0.617 mmol, Intermediate 2: step b) in THF (6.65 mL) at −78° C. was added potassium bis(trimethylsilyl)amide (0.5 M in toluene, 3.66 mL, 1.83 mmol) over 1.5 minutes, and the mixture was stirred for 5 minutes. The dry-ice/acetone bath was replaced with wet-ice bath and the reaction was stirred for 1.5 hours. The reaction was then quenched with water and ethyl acetate was added. The organic layer was removed and the aqueous layer was acidified with 2 N HCl (kept pH above 2). An off-white precipitate was formed which was filtered and the solid was dried overnight in the air and 1 hour in an oven at 40° C. to give the title compound.

Intermediate 2

Step d 4-((6-Bromo-2,4-dichloroquinolin-3-yl)oxy)benzonitrile

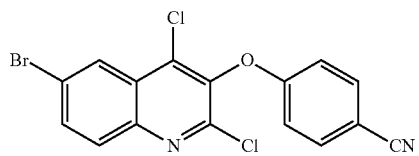 [SMILES: N#Cc1ccc(Oc2c(Cl)nc3ccc(Br)cc3c2Cl)cc1]

To a suspension of 4-((6-bromo-4-hydroxy-2-oxo-1,2-dihydroquinolin-3-yl)oxy)benzonitrile (1.8 g, 5.04 mmol, Intermediate 2: step c) in acetonitrile (10 mL) was added phosphorous oxychloride (2.35 mL, 25.20 mmol) and the mixture was heated to 100° C. overnight. The reaction was concentrated, dichloromethane was added and the organic layer was washed with water, dried (MgSO$_4$), filtered and concentrated. The residue was purified over a silica gel column with ethyl acetate/heptane to give the title compound.

Intermediate 3

4-(((6-Bromo-4-chloro-2-(pyrrolidin-1-yl)quinolin-3-yl)oxy)benzonitrile

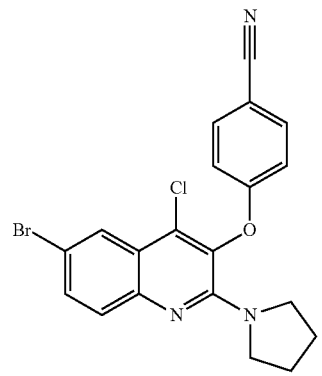 [SMILES: N#Cc1ccc(Oc2c(N3CCCC3)nc3ccc(Br)cc3c2Cl)cc1]

To 4-((6-bromo-2,4-dichloroquinolin-3-yl)oxy)benzonitrile (0.330 g, 0.837 mmol, Intermediate 2: step d) was added N,N-dimethylformamide (3 mL) and pyrrolidine (0.070 mL, 0.837 mmol), and the reaction was heated at 60° C. for 3 hours, followed by heating to 100° C. for 2 hours. An additional 2 equivalents of pyrrolidine (0.140 mL, 1.675 mol) was added and the reaction was heated overnight. The reaction was cooled, diluted with ethyl acetate and the organic layer was washed with water to remove the N,N-dimethylformamide. The organic layer was dried (MgSO$_4$), filtered and concentrated, then purified over a silica gel column with ethyl acetate/heptane to afford the title compound.

Intermediate 4

Step a 6-(Trifluoromethyl)nicotinoyl chloride

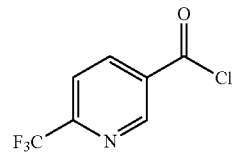 [SMILES: O=C(Cl)c1ccc(C(F)(F)F)nc1]

To a 1 L 3-neck flask equipped with an overhead stirrer, Claisen adaptor, nitrogen bubbler, 60 mL addition funnel, and thermocouple was added 6-(trifluoromethyl)nicotinic acid (45.0 g, 236 mmol), dichloromethane (540 mL) and DMF (0.910 mL, 11.8 mmol) via syringe. To this solution was added oxalyl chloride (24.5 mL, 283 mmol) and the reaction was allowed to stir at ambient temperature overnight. The reaction was then filtered and the clear filtrate was concentrated in vacuo to afford the title compound as a brown semi-solid.

Intermediate 4

Step b

N-methoxy-N-methyl-6-(trifluoromethyl)nicotinamide

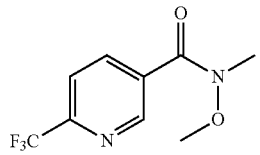 [SMILES: CON(C)C(=O)c1ccc(C(F)(F)F)nc1]

To a 1 L 3-neck flask equipped with an overhead stirrer, Claisen adaptor, nitrogen bubbler, 125 mL addition funnel, and thermocouple was added 6-(trifluoromethyl)nicotinoyl chloride (49.3 g, 235 mmol, Intermediate 4: step a), dichloromethane (493 mL), and N,O-dimethylhydroxylamine hydrochloride (25.63 g, 258.8 mmol). After the mixture was cooled to 7° C., diisopropylethylamine (90.26 mL, 517.6 mmol) was added such that the addition temperature did not exceed 16° C. After the addition, the reaction was allowed to warm to room temperature. The reaction was then transferred to a reparatory funnel and the organic layer was washed with saturated aqueous $NaHCO_3$ (2×100 mL) followed by water (100 mL) and then dried over sodium sulfate and filtered. Removal of solvent afforded a brown oil as the title compound.

Intermediate 4

Step c (1-Methyl-1H-imidazol-5-yl)(6-(trifluoromethyl)pyridin-3-yl)methanone

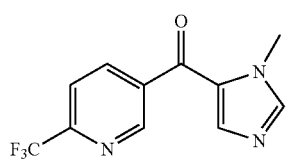 [SMILES: Cn1cncc1C(=O)c1ccc(C(F)(F)F)nc1]

To a 3 L 4-neck flask equipped with an overhead stirrer, nitrogen bubbler, and thermocouple was added 5-bromo-1-methyl-1H-imidazole (47.96 g, 297.9 mmol), followed by THF (537 mL). To this room temperature solution was added isopropylmagnesium chloride/lithium chloride complex (246.8 mL, 320.8 mmol, 1.3 M in THF) (addition temperature maintained between 16.6 and 25° C.) to afford a milky suspension and the reaction was stirred for 60 minutes and then cooled to 5.3° C. in an ice bath. To this mixture was added a solution of N-methoxy-N-methyl-6-(trifluoromethyl)nicotinamide (53.66 g, 229.1 mmol, Intermediate 4: step b) in THF (268 mL) (addition temperature between 5.3 and 5.6° C.) to afford an orange mixture. After addition, the reaction was warmed to room temperature over 2 hours. After stirring at room temperature for 18 hours, THF (200 mL) was added and the reaction was stirred for 2 hours. The reaction was then cooled to 4° C. with an ice bath and carefully quenched with 2 N aqueous HCl to pH=7, quenching temperature reached 12° C. The mixture was diluted with ethyl acetate (500 mL), the phases were separated, and the organic layer was washed with brine (2×200 mL) and dried over sodium sulfate, filtered and the solvent was removed. Hot ether was added and then filtered to give the title compound as a solid.

Intermediate 5

Step a

Methyl 5-bromo-2-(2-phenoxyacetamido)benzoate

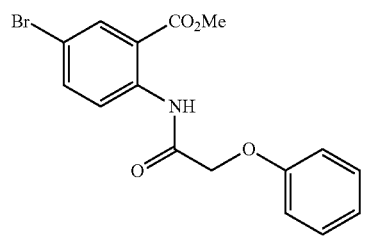 [SMILES: COC(=O)c1cc(Br)ccc1NC(=O)COc1ccccc1]

To a solution of commercially available methyl 2-amino-5-bromobenzoate (10.0 g, 43.5 mmol) in dichloromethane (100 mL) was added 2-phenoxyacetyl chloride (6.60 mL, 47.8 mmol). The white suspension formed was cooled to 0° C. and treated with triethylamine (13.3 mL, 95.6 mmol) dropwise. The resulting solution was stirred at room temperature for 0.5 hours. The mixture was diluted with $CH_2Cl_2$ and was washed with water and saturated aqueous $NH_4Cl$ solution. The organic phase was dried ($MgSO_4$), filtered, and concentrated. The residue was purified by flash column chromatography (silica gel, 7% EtOAc-heptane), to afford the title compound.

Intermediate 5

Step b

6-Bromo-4-hydroxy-3-phenoxyquinolin-2(1H)-one

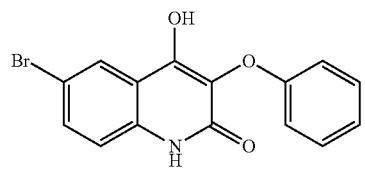 [SMILES: O=c1[nH]c2ccc(Br)cc2c(O)c1Oc1ccccc1]

To a solution of methyl 5-bromo-2-(2-phenoxyacetamido) benzoate (7.28 g, 20.0 mmol, Intermediate 5: step a) in tetrahydrofuran (215 mL) at −78° C. was added potassium bis(trimethylsilyl)amide (0.5 M solution in toluene, 118.7 mL, 59.37 mmol) over 7 minutes. The mixture was stirred at −78° C. for 5 minutes and 0° C. for 1.5 hours. The resulting cold solution was quenched with water. The white solid formed was completely dissolved by addition of excess water. The aqueous phase was washed once with EtOAc and then acidified by slow addition of 2 N aqueous HCl solution (kept pH above 2). The off-white precipitate formed was filtered and dried in the air overnight and at 40° C. for 1 hour to provide the title compound.

Intermediate 5

Step c

6-Bromo-2,4-dichloro-3-phenoxyquinoline

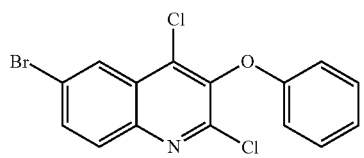 [SMILES: Clc1nc2ccc(Br)cc2c(Cl)c1Oc1ccccc1]

To a suspension of 6-bromo-4-hydroxy-3-phenoxyquinolin-2(1H)-one (4.30 g, 13.0 mmol, Intermediate 5: step b) in CH$_3$CN (30 mL) was added phosphoryl chloride (3.60 mL, 38.8 mmol). The resulting mixture was heated at 100° C. for 16 hours. The dark suspension was cooled to room temperature and filtered. The solid residue was washed with cold MeOH to provide an off-white solid. The filtrate was concentrated to one third of its volume, then a small amount of MeOH was added and cooled to 0° C. to provide a second batch of solid suspension. This was filtered and the residue was washed with cold MeOH. The two batches of solid were combined and dried under vacuum to provide the title compound.

Intermediate 5

Step d

6-Bromo-4-chloro-N,N-diethyl-3-phenoxyquinolin-2-amine

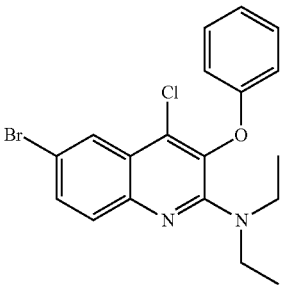 [SMILES: CCN(CC)c1nc2ccc(Br)cc2c(Cl)c1Oc1ccccc1]

A mixture of 6-bromo-2,4-dichloro-3-phenoxyquinoline (2.92 g, 7.91 mmol, Intermediate 5, step c), diethylamine (8.2 mL, 79.1 mmol) and DMF (2 mL) in a sealed tube were heated at 80° C. for 15 hours. The resulting solution was cooled to room temperature and diluted with EtOAc. The organic phase was washed thoroughly with water, dried (MgSO$_4$), filtered and concentrated. The residue was purified by flash column chromatography (silica gel, 5% EtOAc-heptane), affording the title compound.

Intermediate 6

Step a (1-Methyl-1H-imidazol-5-yl)(pyridin-2-yl)methanol

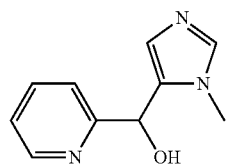

A solution of isopropylmagnesium chloride/lithium chloride complex (1.3 M in THF, 19.5 mL, 25.35 mmol) was added dropwise by syringe to a solution of 5-bromo-1-methyl-1H-imidazole (4.12 g, 25.58 mmol) in dry THF (130 mL) at 0° C. After 15 minutes, the Grignard solution was added via cannulation to a solution of picolinaldehyde (2.0 ml, 20.93 mmol) in dry THF (55 mL) at 0° C. The reaction mixture was stirred for 5 minutes at 0° C., then warmed to room temperature for 1 hour. The reaction mixture was then cooled in an ice bath and quenched with saturated aqueous ammonium chloride. The mixture was partitioned between brine and ethyl acetate. The separated aqueous phase was further extracted with ethyl acetate. The organic phase was dried (Na$_2$SO$_4$), filtered, and concentrated. The crude product was purified by flash column chromatography (silica gel, 0-5% MeOH-DCM) to provide the title compound as a white solid.

Intermediate 6

Step b (1-Methyl-1H-imidazol-5-yl)(pyridin-2-yl)methanone

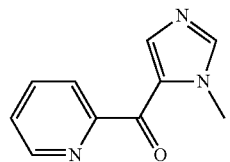

A heterogenous mixture of (1-methyl-1H-imidazol-5-yl)(pyridin-2-yl)methanol (1.41 g, 7.45 mmol, Intermediate 6: step a) and manganese dioxide (3.24 g, 37.27 mmol) in 1,4-dioxane (52 mL) was stirred at 100° C. for 2 hours. The reaction mixture was then allowed to cool to room temperature, filtered through Celite®, rinsed with DCM, and concentrated to provide the title compound as an off-white solid.

Intermediate 7

Step a

Methyl 5-bromo-2-(2-(4-chlorophenoxy)acetamido)benzoate

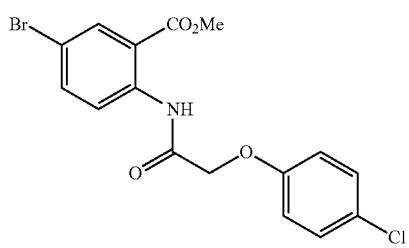 [SMILES: COC(=O)c1cc(Br)ccc1NC(=O)COc1ccc(Cl)cc1]

To a solution of methyl 2-amino-5-bromobenzoate (3.03 mL, 17.4 mmol) in THF (28 mL) was added 2-(4-chlorophenoxy)acetyl chloride (3.92 g, 19.1 mmol) to form a suspension. An additional 30 mL of dichloromethane was added. The reaction was then cooled to 0° C. and triethylamine (5.32 mL, 38.3 mmol) was added dropwise. The cold bath was removed and the reaction was stirred at room temperature for 2 hours. Analysis showed the reaction to be incomplete, so additional 2-(4-chlorophenoxy)acetyl chloride (0.5 mL, 3.22 mmol) was added and reaction solution was stirred for 1 hour then transferred to a reparatory funnel with dichloromethane dilution. The organic phase was washed with water and saturated aqueous NH$_4$Cl solution, then dried (MgSO$_4$), filtered, and concentrated to yield the title compound.

Intermediate 7

Step b

6-Bromo-3-(4-chlorophenoxy)-4-hydroxyquinolin-2(1H)-one

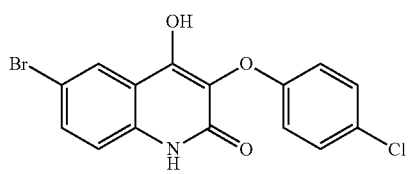 [SMILES: O=c1[nH]c2ccc(Br)cc2c(O)c1Oc1ccc(Cl)cc1]

To a suspension of methyl 5-bromo-2-(2-(4-chlorophenoxy)acetamido)benzoate (5.15 g, 12.9 mmol, Intermediate 7: step a) in THF (140 mL) at −78° C. was added potassium bis(trimethylsilyl)amide (0.5 M in toluene, 76.7 mL, 38.4 mmol) over 4 minutes, and the mixture was stirred for 5 minutes. The dry-ice/acetone bath was replaced an with an ice-water bath and the reaction was stirred for 1.5 hours. The reaction was then quenched with water and ethyl acetate was added. The organic layer was removed and the aqueous layer was acidified with 2 N HCl (kept pH above 2). An off-white precipitate formed which was filtered and the solid was dried overnight in the air to yield the title compound.

Intermediate 7

Step c

6-Bromo-2,4-dichloro-3-(4-chlorophenoxy)quinoline

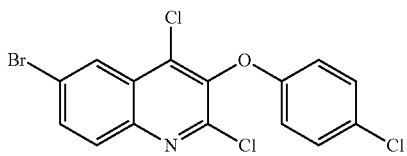 [SMILES: Clc1ccc(Oc2c(Cl)nc3ccc(Br)cc3c2Cl)cc1]

To a suspension of 6-bromo-3-(4-chlorophenoxy)-4-hydroxyquinolin-2(1H)-one (4.59 g, 12.5 mmol, Intermediate 7: step b) in acetonitrile (40 mL) was added phosphorous oxychloride (3.50 mL, 37.6 mmol) and the mixture was heated to 100° C. for 8 hours. The reaction mixture was cooled and the formed precipitate was collected by filtration on a Buchner funnel to yield the first crop of the title compound. The filtrate was subsequently concentrated to approximately one third of its original volume then cooled to 0° C. and the precipitate was collected on a Buchner funnel to yield a second crop of the title compound.

Intermediate 7

Step d

6-Bromo-4-chloro-3-(4-chlorophenoxy)-2-(3-isopropoxyazetidin-1-yl)quinoline

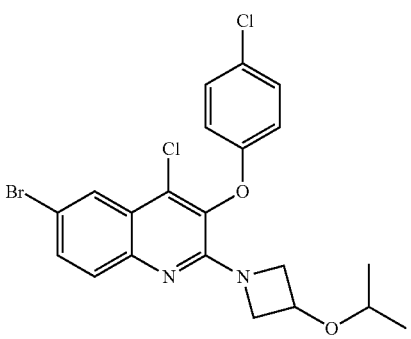 [SMILES: CC(C)OC1CN(c2nc3ccc(Br)cc3c(Cl)c2Oc2ccc(Cl)cc2)C1]

To 6-bromo-2,4-dichloro-3-(4-chlorophenoxy)quinoline (0.50 g, 1.24 mmol, Intermediate 7: step c) was added N,N-dimethylformamide (3 mL) and 3-isopropoxyazetidine-HCl (0.188 g, 1.24 mmol), and the reaction was heated at 60° C. overnight. The reaction was cooled, diluted with ethyl acetate and the organic layer was washed with water five times to remove the N,N-dimethylformamide. The organic layer was dried (MgSO$_4$), filtered and concentrated, then purified over a silica gel column with ethyl acetate/heptane to afford the title compound.

Intermediate 8

Step a

6-Bromo-4-hydroxyquinolin-2(1H)-one

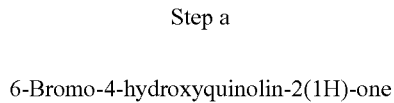

According to the general method described in Synth. Commun. 2010, 40, 732, a mixture of 4-bromoaniline (10.0 g, 58.1 mmol) and 2,2-dimethyl-1,3-dioxan-4,6-dione (8.40 g, 58.1 mmol) was heated at 80° C. for 1 hour and cooled to room temperature to receive 3-((4-bromophenyl)amino)-3-oxopropanoic acid as a solid. A stream of nitrogen gas was passed over the solid product to remove liquid acetone formed as a by-product. To this solid was added Eaton's reagent (40 mL) and the mixture was heated at 70° C. for 12 hours and then cooled to room temperature. To the resulting mixture was added water and stirred vigorously to receive a suspension which was filtered. The solid residue was washed with water and dried in air to yield the title compound.

Intermediate 8

Step b (6-Bromo-4-hydroxy-2-oxo-1,2-dihydroquinolin-3-yl)(phenyl)iodoniumtrifluoromethane sulfonate

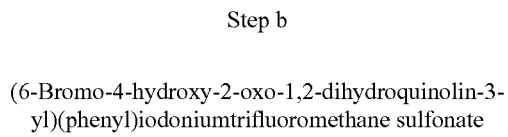

To a suspension of 6-bromo-4-hydroxyquinolin-2(1H)-one (11.0 g, 45.8 mmol, Intermediate 8, step a) and (diacetoxyiodo)benzene (13.4 g, 41.7 mmol) in dichloromethane (180 mL) at 0° C. was added trifluoromethanesulfonic acid (4.06 mL, 45.8 mmol) dropwise. The resulting mixture was stirred in an ice-water bath for 1 hour and at room temperature for 2 hours to receive a suspension which was filtered. The solid product was washed with dichloromethane and dried under vacuum at 50° C. for 12 hours to yield the title compound.

Intermediate 8

Step c

6-Bromo-4-hydroxy-3-(phenylamino)quinolin-2(1H)-one

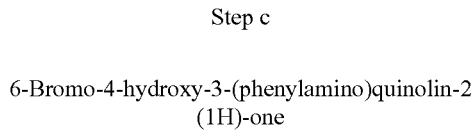

A mixture of (6-bromo-4-hydroxy-2-oxo-1,2-dihydroquinolin-3-yl)(phenyl)iodoniumtrifluoromethane sulfonate (1.40 g, 2.36 mmol, Intermediate 8, step b) and aniline (1 mL) was stirred for 4 hours at room temperature. To this was added DCM and the resulting suspension was filtered. The solid was washed first with DCM followed by water and air dried under vacuum at 50° C. to yield the title compound.

Intermediate 8

Step d

6-Bromo-2,4-dichloro-N-phenylquinolin-3-amine

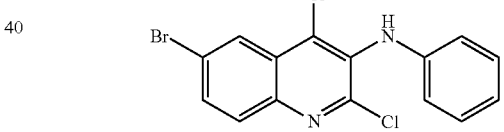

To 6-bromo-4-hydroxy-3-(phenylamino)quinolin-2(1H)-one (648 mg, 1.96 mmol, Intermediate 8, step c) was added phosphoryl trichloride (5 mL, 53.7 mmol) and the mixture was heated at 100° C. for 24 hours. The resulting solution was concentrated in vacuo to remove excess phosphoryl trichloride and the thick liquid that remained was cooled to 4° C. and treated with aqueous ammonium hydroxide (28-30%) dropwise to bring the solution pH between 9-10. To this was added water, and the solution was heated at 40° C. for 0.5 hours and the suspension formed was filtered. The solid, the title compound as phosphoryl amide adduct, was suspended in water, acidified with concentrated aqueous HCl to pH=2 then heated at 50° C. overnight and additionally at 90° C. for 3 hours. The resulting mixture was cooled to room temperature, basified with 3 N aqueous NaOH solution and extracted with EtOAc. The organic phase was separated, dried (MgSO$_4$), filtered and concentrated in vacuo. The residue was purified by flash column chromatography (silica gel, 10% EtOAc-heptane) to yield the title compound.

Intermediate 8

Step e tert-Butyl (6-bromo-2,4-dichloroquinolin-3-yl)(phenyl)carbamate

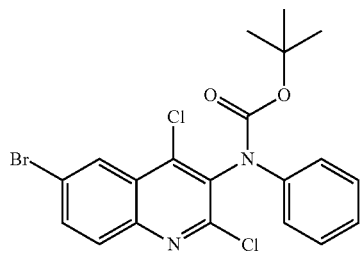 [SMILES: CC(C)(C)OC(=O)N(c1ccccc1)c1c(Cl)nc2ccc(Br)cc2c1Cl]

To a solution of 6-bromo-2,4-dichloro-N-phenylquinolin-3-amine (226 mg, 0.610 mmol, Intermediate 8, step d) in tetrahydrofuran (6 mL) was added di-tert-butyl dicarbonate (214 mg, 0.980 mmol), N,N-dimethylpyridin-4-amine (120 mg, 0.980 mmol) and the mixture was stirred overnight at room temperature. The resulting solution was diluted with EtOAc and the organic phase was washed with saturated aqueous sodium bicarbonate solution followed by brine. The organic phase was dried ($MgSO_4$), filtered and concentrated in vacuo. The residue was purified by flash column chromatography (silica gel, 3% EtOAc-heptane) to yield the title compound.

Example 1

4-((4-chloro-6-((4-chlorophenyl)(hydroxy)(1-methyl-1H-imidazol-5-yl)methyl)-2-(2-oxoazetidin-1-yl)quinolin-3-yl)oxy)benzonitrile• TFA

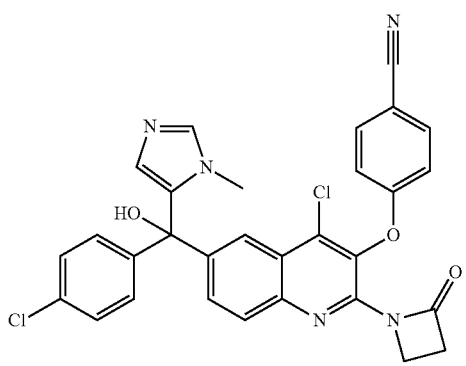 [SMILES: Cn1cncc1C(O)(c1ccc(Cl)cc1)c1ccc2nc(N3CCC3=O)c(Oc3ccc(C#N)cc3)c(Cl)c2c1]

To a flamed dried sealed tube with molecular sieves (33 mg) was added 4-((2,4-dichloro-6-((4-chlorophenyl)(hydroxy)(1-methyl-1H-imidazol-5-yl)methyl)quinolin-3-yl)oxy)benzonitrile (0.049 g, 0.091 mmol, Example 4), tris(dibenzylideneacetone)dipalladium(0) (0.0043 g, 0.0047 mmol), 2-azetidinone (0.009 g, 0.132 mmol), cesium carbonate (0.043 g, 0.130 mmol), and 9,9-dimethyl-4,5-bis(diphenylphosphino)xanthene (0.0098 g, 0.0169 mmol). The flask was covered with a rubber septum and evacuated with vacuum, then purged with nitrogen (repeated three times). Then 1,4-dioxane (1 mL) was added and the tube was sealed. The reaction was then heated at 100° C. overnight. The reaction was then cooled to room temperature, diluted with ethyl acetate and filtered through a pad of Celite®. The Celite® was washed once with methanol and the filtrate was concentrated and purified over a silica gel column with 3% methanol in dichloromethane, followed by reverse-phase purification with water/acetonitrile/0.1% TFA to obtain the product as a trifluoroacetic acid salt.

$^1$H NMR (400 MHz, $CD_3OD$) δ ppm 8.96 (s, 1H), 8.16 (s, 1H), 8.07 (d, J=9.09 Hz, 1H), 7.78 (dd, J=2.02, 8.59 Hz, 1H), 7.71 (d, J=9.09 Hz, 2H), 7.53-7.33 (m, 4H), 7.02 (d, J=9.09 Hz, 2H), 6.94 (s, 1H), 3.90 (t, J=5.05 Hz, 2H), 3.69 (s, 3H), 3.05 (t, 2H); MS m/e 570.2 $[M+H]^+$.

Example 2a 4-((4-Chloro-6-(hydroxy(1-methyl-1H-imidazol-5-yl)(6-(trifluoromethyl)pyridin-3-yl)methyl)-2-(pyrrolidin-1-yl)quinolin-3-yl)oxy)benzonitrile

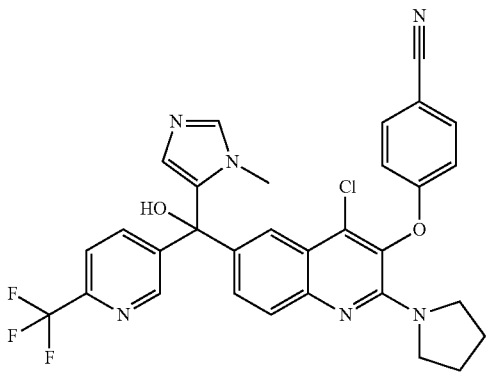 [SMILES: Cn1cncc1C(O)(c1ccc(C(F)(F)F)nc1)c1ccc2nc(N3CCCC3)c(Oc3ccc(C#N)cc3)c(Cl)c2c1]

To 4-((6-bromo-4-chloro-2-(pyrrolidin-1-yl)quinolin-3-yl)oxy)benzonitrile (0.22 g, 0.52 mmol, Intermediate 3) in THF (3 mL) at −78° C. was added n-BuLi [1.6 M in hexanes] (0.390 mL, 0.624 mmol) dropwise and stirred for 5 minutes. To the resulting solution was added (1-methyl-1H-imidazol-5-yl)(6-(trifluoromethyl)pyridin-3-yl)methanone (0.159 g, 0.624 mmol, Intermediate 4: step c) in THF (2.2 mL) and the reaction was stirred for 5 min at −78° C. The dry-ice bath was replaced with wet-ice bath and the reaction was stirred for 30 minutes while it warmed to 0° C. The reaction was then quenched with water, ethyl acetate was added and the organic layer was washed with water. The organic phase was dried ($MgSO_4$), filtered, concentrated and purified over a silica gel column with dichloromethane/methanol, followed by reverse-phase purification with water/acetonitrile/0.1% TFA to obtain the product as a trifluoroacetic acid salt. The fractions were combined and concentrated, ethyl acetate was added, followed by saturated aqueous $NaHCO_3$ solution. The phases were separated and the organic phase was washed with water. The organic phase was dried ($MgSO_4$), filtered and concentrated to give the title compound. $^1$H NMR (400 MHz, $CD_3OD-d_4$) δ ppm 9.01 (s, 1H), 8.79 (d, J=2.02 Hz, 1H), 8.07 (d, J=8.08 Hz, 1H), 8.00 (bs, 1H), 7.88 (d, J=8.08 Hz, 1H), 7.87-7.77 (m, 1H), 7.73 (d, J=8.08 Hz, 2H), 7.58 (bs, 1H), 7.09-6.97 (m, 3H), 3.73-3.68 (m, 7H), 1.96-1.87 (m, 4H); MS m/e 605.3 $[M+H]^+$.

Example 2a was purified by supercritical fluid chromatography (SFC) (Daicel Chiralpak AD-H, 5 micrometer, UV 254 nm, 50° C., 50 mL/minute) using an isocratic mixture of CO₂/methanol+0.2% isopropylamine: 85/15. The first eluting enantiomer was then further purified over a silica gel column with 8% methanol in dichloromethane, concentrated, dissolved in THF (6 mL) and 2.2 equivalents of 1M aqueous HCl in diethyl ether was added to the solution, then the solution was concentrated and dried in vacuo to give Example 2b.HCl. $^1$H NMR (400 MHz, CD₃OD) δ ppm 9.01 (s, 1H), 8.79 (d, J=2.02 Hz, 1H), 8.15-8.03 (m, 1H), 8.00 (s, 1H), 7.88 (d, J=8.59 Hz, 1H), 7.83 (d, J=9.09 Hz, 1H), 7.73 (d, J=8.59 Hz, 2H), 7.59 (d, J=7.07 Hz, 1H), 7.06 (s, 1H), 7.02 (d, J=8.59 Hz, 2H), 3.76-3.63 (m, 7H), 1.96-1.86 (m, 4H); MS m/e 605.3 [M+H]⁺. The second eluting enantiomer was then further purified over a silica gel column with 8% methanol in dichloromethane, concentrated, dissolved in THF (6 mL) and 2.2 equivalents of 1M aqueous HCl in diethyl ether was added to the solution, then the solutions were concentrated and dried in vacuo to give Example 2c.HCl. $^1$H NMR (400 MHz, CD₃OD) δ ppm 9.03 (s, 1H), 8.79 (s, 1H), 8.13-8.02 (m, 2H), 7.95-7.84 (m, 2H), 7.75 (d, J=8.59 Hz, 2H), 7.65 (d, J=8.59 Hz, 1H), 7.14-7.00 (m, 3H), 3.80-3.72 (m, 4H), 3.70-3.73 (m, 3H), 2.01-1.90 (m, 4H); MS m/e 605.3 [M+H]⁺.

Example 3a (4-Chloro-2-(diethylamino)-3-phenoxyquinolin-6-yl)(1-methyl-1H-imidazol-5-yl)(pyridin-2-yl)methanol

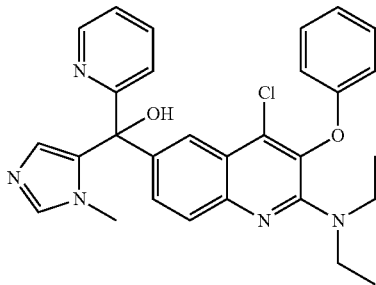 [SMILES: CCN(CC)c1nc2ccc(C(O)(c3ccccn3)c3cncn3C)cc2c(Cl)c1Oc1ccccc1]

A solution of n-BuLi (2.5 M in hexanes, 0.49 mL, 1.2 mmol) was added dropwise by syringe to a solution of 6-bromo-4-chloro-N,N-diethyl-3-phenoxyquinolin-2-amine (0.500 g, 1.23 mmol, Intermediate 5: step d) in dry THF (20.5 mL) in a dry ice-acetone bath. After 1-2 minutes, a solution of (1-methyl-1H-imidazol-5-yl)(pyridin-2-yl)methanone (230.9 mg, 1.233 mmol, Intermediate 6: step b) in dry THF (1.5 mL) was added dropwise. The reaction was stirred for 2 minutes, then moved into an ice bath for 7 minutes, and finally allowed to warm to ambient temperature for 1 hour. The reaction was quenched with saturated aqueous ammonium chloride. The mixture was partitioned between water/brine and dichloromethane. The separated aqueous phase was further extracted with dichloromethane. The organic phase was dried (Na₂SO₄), filtered, and concentrated. The crude product was purified by flash column chromatography (silica gel, 100% EtOAc), followed by reverse phase chromatography (ACN/H₂0+0.05% TFA). Product fractions were basified with saturated aqueous sodium bicarbonate and extracted with DCM, before being dried (Na₂SO₄), filtered, and concentrated to provide the title compound. $^1$H NMR (500 MHz, DMSO-d₆) δ ppm 8.54 (d, J=3.9 Hz, 1H), 8.05 (d, J=1.6 Hz, 1H), 7.84 (dd, J=9.5, 7.7 Hz, 1H), 7.66 (d, J=1.8 Hz, 1H), 7.65 (s, 1H), 7.59 (s, 1H), 7.32 (dd, J=14.1, 5.4 Hz, 3H), 7.05 (t, J=7.3 Hz, 1H), 6.93 (s, 1H), 6.79 (d, J=7.8 Hz, 2H), 6.22 (d, J=1.1 Hz, 1H), 3.51 (q, J=14.6, 7.3 Hz, 4H), 3.25 (s, 3H), 1.05 (t, J=7.0 Hz, 6H); MS m/e 514.3 [M+H]⁺.

Example 3a was purified by chiral HPLC (ChiralPak OD, 80:20 heptane/EtOH) to provide two pure enantiomers. The first eluting enantiomer is Example 3b: $^1$H NMR (400 MHz, CDCl₃) δ ppm 8.62 (d, J=4.8 Hz, 1H), 7.93 (d, J=2.0 Hz, 1H), 7.74-7.70 (m, 1H), 7.70-7.66 (m, 1H), 7.58 (dd, J=8.7, 2.1 Hz, 1H), 7.48 (s, 1H), 7.32-7.21 (m, 3H), 7.06-7.00 (m, 1H), 6.80-6.78 (m, 1H), 6.78-6.76 (m, 1H), 6.61 (s, 1H), 6.33 (s, 1H), 3.56 (q, J=7.0 Hz, 4H), 3.45 (s, 3H), 1.11 (t, J=7.0 Hz, 6H); MS m/e 514.2 [M+H]⁺. The second eluting enantiomer is Example 3c: $^1$H NMR (400 MHz, CDCl₃) δ ppm 8.61 (d, J=4.8 Hz, 1H), 7.94 (d, J=2.1 Hz, 1H), 7.74-7.70 (m, 1H), 7.70-7.65 (m, 1H), 7.58 (dd, J=8.8, 2.1 Hz, 1H), 7.51 (s, 1H), 7.32-7.21 (m, 3H), 7.02 (t, J=7.4 Hz, 1H), 6.80-6.78 (m, 1H), 6.78-6.76 (m, 1H), 6.61 (s, 1H), 6.34 (s, 1H), 3.56 (q, J=7.0 Hz, 4H), 3.45 (s, 3H), 1.11 (t, J=7.0 Hz, 6H); MS m/e 514.2 [M+H]⁺.

Example 4

4-((2,4-Dichloro-6-((4-chlorophenyl)(hydroxy)(1-methyl-1H-imidazol-5-yl)methyl)quinolin-3-yl)oxy)benzonitrile

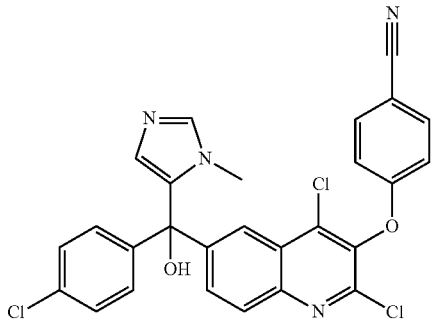 [SMILES: Cn1cncc1C(O)(c1ccc(Cl)cc1)c1ccc2nc(Cl)c(Oc3ccc(C#N)cc3)c(Cl)c2c1]

To 4-((6-bromo-2,4-dichloroquinolin-3-yl)oxy)benzonitrile (0.350 g, 0.888 mmol, Intermediate 2: step d) and (4-chlorophenyl)(1-methyl-1H-imidazol-5-yl)methanone (0.274 g, 1.24 mmol, Intermediate 1: step b) was added THF (12 mL) to form a solution. The reaction was cooled to −78° C. and became a white suspension, then n-BuLi [1.6 M in hexanes] (0.78 mL, 1.2 mmol) was added via a syringe. The reaction was stirred for 15 minutes at −78° C. The dry-ice bath was then replaced with a wet-ice bath and stirred for 15 minutes while it warmed to 0° C. The reaction was then quenched with water, ethyl acetate was added and the organic layer was washed with water. The organic phase was dried (MgSO₄), filtered, concentrated, then purified over a silica gel column with 6% methanol in dichloromethane to give the title compound. $^1$H NMR (400 MHz, CD₃OD) δ ppm 8.26-8.23 (m, 1H), 8.07-8.03 (m, 1H), 7.89-7.85 (m, 1H), 7.83-7.82 (m, 2H), 7.76-7.71 (m, 2H), 7.68-7.67 (m, 1H), 7.38-7.36 (m, 2H), 7.10-7.05 (m, 2H), 6.34-6.32 (m, 1H), 3.48 (s, 3H); MS m/e 535.05 [M+H]⁺.

Example 5a 2-(Diethylamino)-6-(hydroxy(1-methyl-1H-imidazol-5-yl)(pyridin-2-yl)methyl)-3-phenoxyquinoline-4-carbonitrile

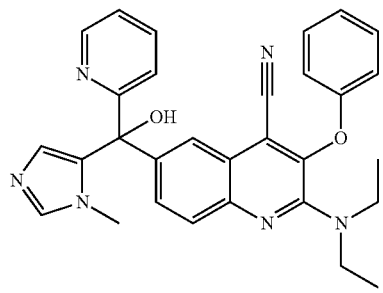 [SMILES: CCN(CC)c1nc2ccc(C(O)(c3ccccn3)c3cncn3C)cc2c(C#N)c1Oc1ccccc1]

(4-Chloro-2-(diethylamino)-3-phenoxyquinolin-6-yl)(1-methyl-1H-imidazol-5-yl)(pyridin-2-yl)methanol (170 mg, 0.165 mmol, Example 3a), zinc cyanide (24.5 mg, 0.209 mmol), zinc dust (7.6 mg, 0.116 mmol), X-Phos (9.1 mg, 0.0185 mmol), and $Pd_2(dba)_3$ (16.1 mg, 0.0176 mmol) were charged to an oven-dried microwave vial. The vial was evacuated and back-filled with nitrogen. Dimethylacetamide (1 mL) was sparged with argon and added to the mixture via syringe. Nitrogen was bubbled through the reaction mixture for 5 minutes and the mixture was heated at 120° C. for 4 hours. The mixture was allowed to cool to ambient temperature, filtered through Celite®, and rinsed with ethyl acetate. The filtrate was concentrated and the crude product was purified by reverse-phase chromatography ($ACN/H_2O$+0.05% TFA). Product fractions were basified with saturated aqueous sodium bicarbonate and extracted with DCM. The combined organic layers were dried ($Na_2SO_4$), filtered, and concentrated to provide the title compound. $^1$H NMR (500 MHz, $CDCl_3$) δ ppm 8.64-8.61 (m, 1H), 7.88 (d, J=2.0 Hz, 1H), 7.75 (d, J=8.8 Hz, 1H), 7.70 (td, J=7.7, 1.7 Hz, 1H), 7.64 (dd, J=8.8, 2.1 Hz, 1H), 7.47 (s, 1H), 7.32-7.27 (m, 3H), 7.22 (dt, J=7.9, 1.1 Hz, 1H), 7.11-7.06 (m, 1H), 6.85-6.80 (m, 2H), 6.57 (s, 1H), 6.35 (s, 1H), 3.58 (q, J=7.0 Hz, 4H), 3.43 (s, 3H), 1.12 (t, J=7.0 Hz, 6H); MS m/e 505.4 $[M+H]^+$.

Example 5a was purified by chiral SFC (ChiralPak AD, 75:25 $CO_2$/iPrOH (+0.6% $iPrNH_2$)) to provide two pure enantiomers. The first eluting enantiomer was Example 5b: $^1$H NMR (400 MHz, $CDCl_3$) δ ppm 8.64-8.61 (m, 1H), 7.88 (d, J=1.9 Hz, 1H), 7.75 (d, J=8.8 Hz, 1H), 7.71 (td, J=7.7, 1.7 Hz, 1H), 7.63 (dd, J=8.8, 2.1 Hz, 1H), 7.48 (s, 1H), 7.33-7.27 (m, 3H), 7.22 (d, J=7.9 Hz, 1H), 7.11-7.06 (m, 1H), 6.85-6.81 (m, 2H), 6.58 (s, 1H), 6.35 (s, 1H), 3.58 (q, J=7.1 Hz, 4H), 3.43 (s, 3H), 1.12 (t, J=7.0 Hz, 6H); MS m/e 505.3 $[M+H]^+$. The second eluting enantiomer was Example 5c: $^1$H NMR (400 MHz, $CDCl_3$) δ ppm 8.65-8.60 (m, 1H), 7.88 (d, J=1.8 Hz, 1H), 7.75 (d, J=8.8 Hz, 1H), 7.71 (td, J=7.7, 1.7 Hz, 1H), 7.63 (dd, J=8.8, 2.1 Hz, 1H), 7.48 (s, 1H), 7.33-7.27 (m, 3H), 7.22 (d, J=7.9 Hz, 1H), 7.11-7.06 (m, 1H), 6.85-6.81 (m, 2H), 6.58 (s, 1H), 6.35 (s, 1H), 3.58 (q, J=7.1 Hz, 4H), 3.43 (s, 3H), 1.12 (t, J=7.0 Hz, 6H); MS m/e 505.3 $[M+H]^+$.

Example 6

(4-Chloro-3-(4-chlorophenoxy)-2-(3-isopropoxyazetidin-1-yl)quinolin-6-yl)(1-methyl-1H-imidazol-5-yl)(6-(trifluoromethyl)pyridin-3-yl)methanol

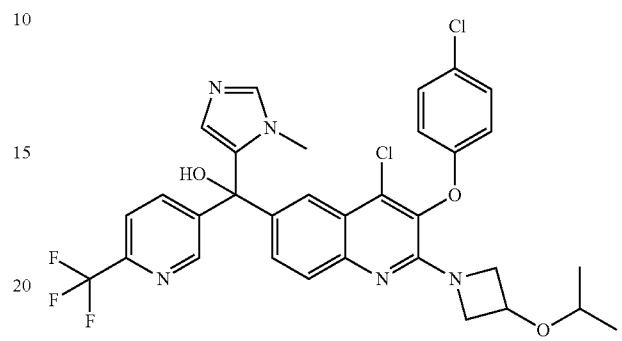

To 6-bromo-4-chloro-3-(4-chlorophenoxy)-2-(3-isopropoxyazetidin-1-yl)quinoline (0.35 g, 0.72 mmol, Intermediate 7: step d) in THF (7 mL) at −78° C. was added n-BuLi (1.6 M in hexanes, 0.58 mL, 0.93 mmol) dropwise and stirred for 5 minutes. To the resulting solution was added (1-methyl-1H-imidazol-5-yl)(6-(trifluoromethyl)pyridin-3-yl)methanone (0.22 g, 0.86 mmol, Intermediate 4: step c) and the reaction was stirred for 5 min at −78° C. The dry-ice bath was replaced with an ice-water bath and the reaction was stirred for 30 minutes at 0° C. Contents were then re-cooled to −78° C. and additional n-BuLi (1.6 M in hexanes, 0.58 mL, 0.93 mmol and (1-methyl-1H-imidazol-5-yl)(6-(trifluoromethyl)pyridin-3-yl)methanone (0.22 g, 0.86 mmol, Intermediate 4: step c) were added and the reaction stirred for 5 minutes. The dry-ice bath was replaced with an ice-water bath and the reaction was stirred for an additional 30 minutes at 0° C. then quenched with water. The reaction solution was transferred to a separatory funnel with ethyl acetate dilution, washed with water, separated, dried ($MgSO_4$), filtered and concentrated. The crude product was purified by flash column chromatography with dichloromethane/methanol, followed by reverse-phase purification with water/acetonitrile/0.1% TFA to obtain the product as a trifluoroacetic acid salt. The fractions containing the desired product were combined and concentrated, then re-dissolved in ethyl acetate and washed with a saturated aqueous $NaHCO_3$ solution and water. The organic phase was dried ($MgSO_4$), filtered and concentrated to give the title compound. $^1$H NMR (400 MHz, $CD_3OD$) δ ppm 8.76 (d, J=2.1 Hz, 1H), 8.00 (dd, J=8.3, 2.3 Hz, 1H), 7.96 (d, J=2.2 Hz, 1H), 7.82 (d, J=8.3 Hz, 1H), 7.76 (d, J=8.9 Hz, 1H), 7.72 (s, 1H), 7.57 (dd, J=8.9, 2.2 Hz, 1H), 7.37-7.28 (m, 2H), 6.86-6.79 (m, 2H), 6.34 (s, 1H), 4.48-4.35 (m, 3H), 4.05-3.97 (m, 2H), 3.69-3.59 (m, 1H), 3.48 (s, 3H), 1.12 (d, J=6.1 Hz, 6H); MS m/e 658.2 $[M+H]^+$.

Example 7 tert-Butyl (2,4-dichloro-6-((3-chlorophenyl)(hydroxy)(pyridin-3-yl)methyl)quinolin-3-yl)(phenyl)carbamate

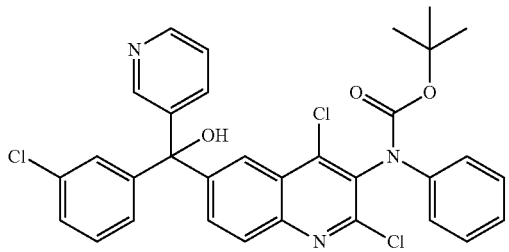 [SMILES: CC(C)(C)OC(=O)N(c1ccccc1)c1c(Cl)nc2ccc(C(O)(c3cccnc3)c3cccc(Cl)c3)cc2c1Cl]

To a solution of tert-butyl (6-bromo-2,4-dichloroquinolin-3-yl)(phenyl)carbamate (60 mg, 0.13 mmol, Intermediate 8, step e) and (3-chlorophenyl)(pyridin-3-yl)methanone (31 mg, 0.14 mmol) in tetrahydrofuran (1 mL) at −78° C. was added n-butyllithium (1.6 M solution in hexanes, 0.10 mL, 0.17 mmol) dropwise and stirred at this temperature for 10 minutes then at room temperature for 2 hours. Analysis showed the reaction to be incomplete and hence additional aliquots of reagents were added. The resulting solution was cooled back to −78° C. and treated with (3-chlorophenyl)(pyridin-3-yl)methanone (10 mg, 0.05 mmol) and n-butyllithium (1.6 M solution in hexanes, 0.050 mL, 0.080 mmol) drop wise and stirred at this temperature for 1 hour and then allowed to warm and stir at room temperature overnight. Analysis showed the reaction to be incomplete and hence additional aliquots of reagents were added again. The reaction solution was cooled back to −78° C. and treated with n-butyllithium (1.6 M solution in hexanes, 0.10 mL, 0.16 mmol) drop wise and stirred at this temperature for 4 hours. Analysis showed the reaction to be incomplete and hence additional aliquots of reagents were again to push the reaction to completion. The reaction solution was treated with (3-chlorophenyl)(pyridin-3-yl)methanone (20 mg, 0.09 mmol) and n-butyllithium (1.6 M solution in hexanes, 0.10 mL, 0.16 mmol) drop wise and stirred at this temperature for 3 hours. The resulting solution was quenched with water and diluted with EtOAc. The organic phase was separated, dried ($MgSO_4$), filtered and concentrated. The residue was purified by flash column chromatography (silica gel, 50% EtOAc-heptane) to yield the title compound. $^1$H NMR (400 MHz, $CDCl_3$) δ ppm 8.58 (s, 2H), 8.16 (d, J=2.1 Hz, 1H), 8.03 (d, J=8.7 Hz, 1H), 7.75-7.62 (m, 2H), 7.38-7.28 (m, 8H), 7.16 (t, J=4.9 Hz, 2H), 1.43 (s, 9H); MS m/e 607.1 [M+H]$^+$.

In Vitro Biological Data
ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM_001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor assay is shown as SEQ ID NO:4.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 μL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 μM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1×=46 nL) using a Hummingbird capillary liquid handling instrument (Digilab). Following compound dispense, protein and dye in buffer was added to achieve the final assay volume of 3 μL, followed by 1 μL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt $T_m$: 47.8° C.
$\Delta H_{(Tm)}$=115 kcal/mol
$\Delta C_{p(Tm)}$=3 kcal/mol Cell Based Biological Data RORγt Reporter Assay A reporter assay was used to test functional activity of RORγt modulatory compounds on transcriptional activation driven by the RORγt LBD. Cells used in the assay were co-transfected with two constructs. The first construct, pBIND-RORγt LBD, contained the wild type human RORγt LBD fused to the DNA binding domain of the GAL4 protein. The second construct, pGL4.31 (Promega Cat no. C935A), contained multiple GAL4 responsive DNA elements upstream of firefly luciferase. To generate a background control, cells were similarly co-transfected with two constructs, but in the first construct the AF2 amino acid motif in the RORγt LBD was changed from LYKELF (SEQ ID NO:5) to LFKELF (SEQ ID NO:6). The AF2 mutation has been shown to prevent co-activator binding to the RORγt LBD, thus preventing transcription of firefly luciferase. The mutant construct was called pBIND-RORγt-AF2.

For the RORγt constructs used in the reporter assay, numbering for the nucleotide sequences was also based on the reference sequence for human RORγt, transcript variant 2, NCBI Accession: NM_001001523.1 (SEQ ID NO:1). For the wild type human RORγt LBD construct, pBIND-RORγt LBD, nucleotides 850-1635 (SEQ ID NO:2) coding for the wild type human RORγt LBD were cloned into EcoRI and NotI sites in the pBIND vector (Promega cat. No E245A). The pBIND vector contains the GAL4 DNA Binding Domain (GAL4 DBD) and the renilla luciferase gene under control of the SV40 promoter. Renilla luciferase expression serves as a control for transfection efficiency and cell viability. For the background control construct, pBIND-RORγt-AF2, the AF2 domain of RORγt LBD was mutated using the Quik Change II Site Directed Mutagenesis System (Stratagene Cat. No. 200519). The nucleotide sequence coding for the RORγt LBD sequence with the mutated AF2 domain is shown as SEQ ID NO:7. The amino acid sequences for the wild type RORγt LBD and RORγt LBD with the mutated AF2 domain are shown as SEQ ID NO:8 and SEQ ID NO:9, respectively.

The reporter assay was performed by transiently transfecting HEK293T cells with 5 μg of pBIND-RORγt LBD or pBIND-RORγt LBD-AF2 and 5 μg pGL4.31 (Promega Cat no. C935A) using Fugene 6 (Invitrogen Cat no. E2691) at a 1:6 ratio of DNA: Fugene 6 in a T-75 flask in which cells were at least 80% confluent. Twenty four hours after bulk transfection, cells were plated into 96-well plates at 50,000 cells/well in phenol-red free DMEM containing 5% Lipid Reduced FCS and Pen/Strep. Six hours after plating, cells were treated with compounds for 24 hours. Media was removed and cells were lysed with 50 μL 1× Glo Lysis Buffer (Promega). Dual Glo Luciferase Reagent (50 μL/well) was then added and firefly luciferase luminescence was read on an Envision after a ten minute incubation. Finally, Stop and Glo reagent (50 μL/well) was added and renilla luciferase luminescence was read on an Envision after a ten minute incubation. To calculate the effect of compounds on RORγt activity, the ratio of firefly to renilla luciferase was determined and plotted against compound concentration. Agonist compounds increase RORγt-driven luciferase expression, and antagonist or inverse agonist compounds decrease luciferase expression.

Human Th17 Assay

The human Th17 assay tests the effect of RORγt modulatory compounds on IL-17 production by CD4 T cells under conditions which favor Th17 differentiation.

Total CD4$^+$ T cells were isolated from the peripheral blood mononuclear cells (PBMC) of healthy donors using a CD4$^+$ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at 1.5×10$^5$ per 100 μL per well. 50 μL of compound at titrated concentrations in DMSO were added into each well at final DMSO concentration at 0.2%. Cells were incubated for 1 hour, then 50 μL of Th17 cell differentiation medium was added to each well. The final concentrations of antibodies and cytokines (R&D Systems) in differentiation medium were: 3×10$^6$/mL anti-CD3/CD28 beads (prepared using human T cell activation/expansion kit, Miltenyi Biotec), 10 μg/mL anti-IL4, 10 μg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% $CO_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example Number | ThermoFluor ® Assay, Kd (μM) | RORγt reporter Assay, IC50 (μM) | RORγt reporter Assay, % inhibition @ 6 μM | Human Th17 Assay, $IC_{50}$ (μM) |
|---|---|---|---|---|
| 1 | 0.058 | 0.18 | 101 | 0.3 |
| 2a | 0.066 | 0.28 | 99 | 0.088 |
| 2b | 0.15 | 0.29 | 97 | 0.32 |
| 2c | 0.022 | 0.046 | 96 | 0.1 |
| 3a | ND | ND | ND | ND |
| 3b | 0.14 | 0.2 | 101 | 0.18 |
| 3c | 0.46 | 1.1 | 101 | ND |
| 4 | ND | ND | ND | ND |
| 5a | ND | ND | ND | ND |
| 5b | ND | 0.87 | 102 | ND |
| 5c | >63 | 0.27 | 103 | 0.15 |
| 6 | 11 | >6 | 41 | ND |
| 7 | 23 | 1.4 | 72 | ND |

All data shown in Table 1 is either the value of one data point or the average of more than one data point.
ND—no data.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

What is claimed is:

1. A compound of Formula I

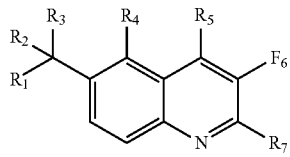

Formula I wherein:
- $R^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, $C(O)CH_3$, $C(O)NH_2$, $CH_3$, $CH_2CH_3$, $CF_3$, Cl, F, —CN, $OCH_3$, $N(CH_3)_2$, —$(CH_2)_3OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups; and wherein said azetidinyl is optionally substituted with $CO_2C(CH_3)_3$, $C(O)NH_2$, $CH_3$, $SO_2CH_3$, or $C(O)CH_3$;
- $R^2$ is 1-methyl-1,2,3-triazolyl, pyridyl, pyridyl-N-oxide, 1-methyl pyrazol-4-yl, pyrimidin-5-yl, pyridazyl, pyrazin-2-yl, oxazolyl, isoxazolyl, N-acetyl-azetidin-3-yl, N-methylsulfonyl-azetidin-3-yl, N-Boc-azetidin-3-yl, N-methyl-azetidin-3-yl, N-acetamidyl-azetidin-3-yl, N-acetyl piperidinyl, 1-H-piperidinyl, N-Boc-piperidinyl, N—$C_{(1-2)}$alkyl-piperidinyl, thiazol-5-yl, 1(3-methoxypropyl)-imidazol-5-yl, or 1-$C_{(1-2)}$ alkyl imidazol-5-yl; wherein said 1-$C_{(1-2)}$alkyl imidazol-5-yl is optionally substituted with up to two additional $CH_3$ groups, or one substituent selected from the group consisting of $SCH_3$, and Cl; and said pyridyl, and pyridyl-N-oxide are optionally substituted with up to two substituents independently selected from the group consisting of $C(O)NH_2$, —CN, $OCH_3$, $CF_3$, Cl, and $CH_3$; and said thiazol-5-yl, oxazolyl, and isoxazolyl are optionally substituted with up to two $CH_3$ groups; and said 1-methyl pyrazol-4-yl is optionally substituted with up to two additional $CH_3$ groups;
- $R^3$ is H, OH, $OCH_3$, $NHCH_3$, $N(CH_3)_2$, or $NH_2$;
- $R^4$ is H, or F;
- $R^5$ is H, Cl, —CN, $CF_3$, $SCH_3$, $OC_{(1-3)}$alkyl, OH, $C_{(1-4)}$alkyl, $N(CH_3)OCH_3$, $NH(C_{(1-2)}$alkyl),$N(C_{(1-2)}$ alkyl)$_2$, NH-cyclopropyl, $OCHF_2$, 4-hydroxy-piperidinyl, azetidin-1-yl, or fur-2-yl;
- $R^6$ is —O-phenyl, —NHphenyl, —N($C_{(1-3)}$alkyl)phenyl, —N($CO_2C(CH_3)_3$)phenyl, —O-pyridyl, —NHpyridyl, —N($C_{(1-3)}$alkyl)pyridyl, or —N($CO_2C(CH_3)_3$)pyridyl wherein said phenyl portions thereof or said pyridyl portions thereof are optionally substituted with $OCF_3$, $SO_2CH_3$, $CF_3$, $CHF_2$, imidazol-1-yl, pyrazol-1-yl, 1,2,4-triazol-1-yl, $CH_3$, $OCH_3$, Cl, F, or —CN;
- $R^7$ is H, Cl, —CN, $C_{(1-4)}$alkyl, $OCH_2CF_3$, $OCH_2CH_2OCH_3$, $CF_3$, $SCH_3$, $SO_2CH_3$, $OCHF_2$, $NA^1A^2$, $C(O)NHCH_3$, $N(CH_3)CH_2CH_2NA^1A^2$, $OCH_2CH_2NA^1A^2$, $OC_{(1-3)}$alkyl, $OCH_2$-(1-methyl)-imidazol-2-yl, imidazol-2-yl, fur-2-yl, pyrazol-4-yl, pyrid-3-yl, or pyrimidin-5-yl; thiophen-3-yl, 1-methyl-indazol-5-yl, 1-methyl-indazol-6-yl, phenyl, or

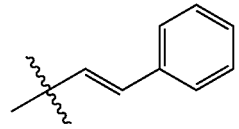 [SMILES: */C=C/c1ccccc1]

wherein said imidazolyl or pyrazolyl can be optionally substituted with a $CH_3$ group;
- $A^1$ is H or $C_{(1-4)}$alkyl;
- $A^2$ is H, $C_{(1-4)}$alkyl, cyclopropyl, $C_{(1-4)}$alkyl$OC_{(1-4)}$alkyl, $C_{(1-4)}$alkylOH, $C(O)C_{(1-2)}$alkyl, or $OCH_3$; or $A^1$ and $A^2$ may be taken together with their attached nitrogen to form a ring selected from the group consisting of:

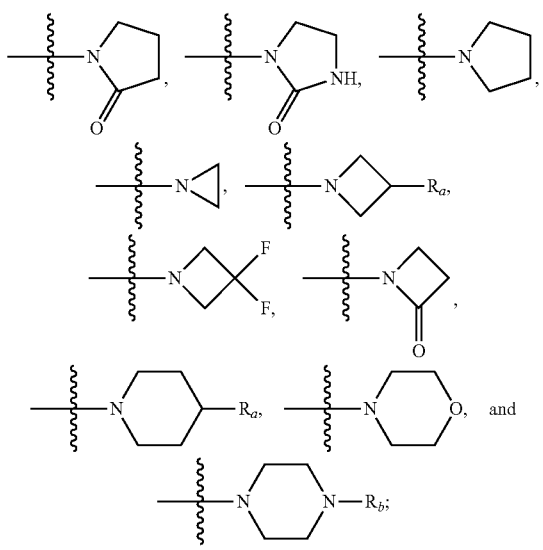

R$_a$ is H, F, OC$_{(1-3)}$alkyl, or OH;
R$_b$ is CH$_3$, or phenyl;
R$^8$ is H, CH$_3$, OCH$_3$, or F;
R$^9$ is H, or F;
and pharmaceutically acceptable salts thereof.

2. A compound of claim 1 wherein:
R$^1$ is 6-trifluoromethyl pyrid-3-yl, pyrid-2-yl, 4-chlorophenyl, or 3-chlorophenyl;
R$^2$ is 1-methyl imidazol-5-yl, or pyrid-3-yl;
R$^3$ is OH;
R$^4$ is H;
R$^5$ is Cl, or —CN;
R$^6$ is —O-phenyl, or —N(CO$_2$C(CH$_3$)$_3$)phenyl, wherein said —O-phenyl is optionally substituted with —CN, or Cl;
R$^7$ is Cl, NA$^1$A$^2$;
A$^1$ is CH$_2$CH$_3$;
A$^2$ is CH$_2$CH$_3$; or A$^1$ and A$^2$ may be taken together with their attached nitrogen to form a ring selected from the group consisting of:

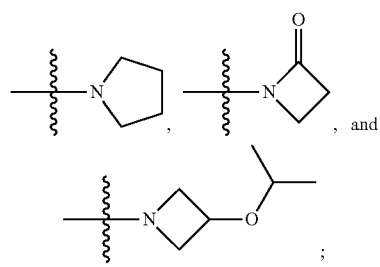

and pharmaceutically acceptable salts thereof.

3. A compound of claim 1 selected from the group consisting of:

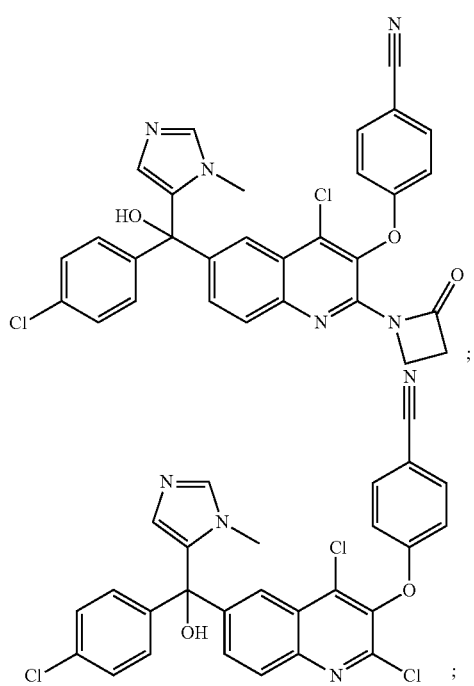

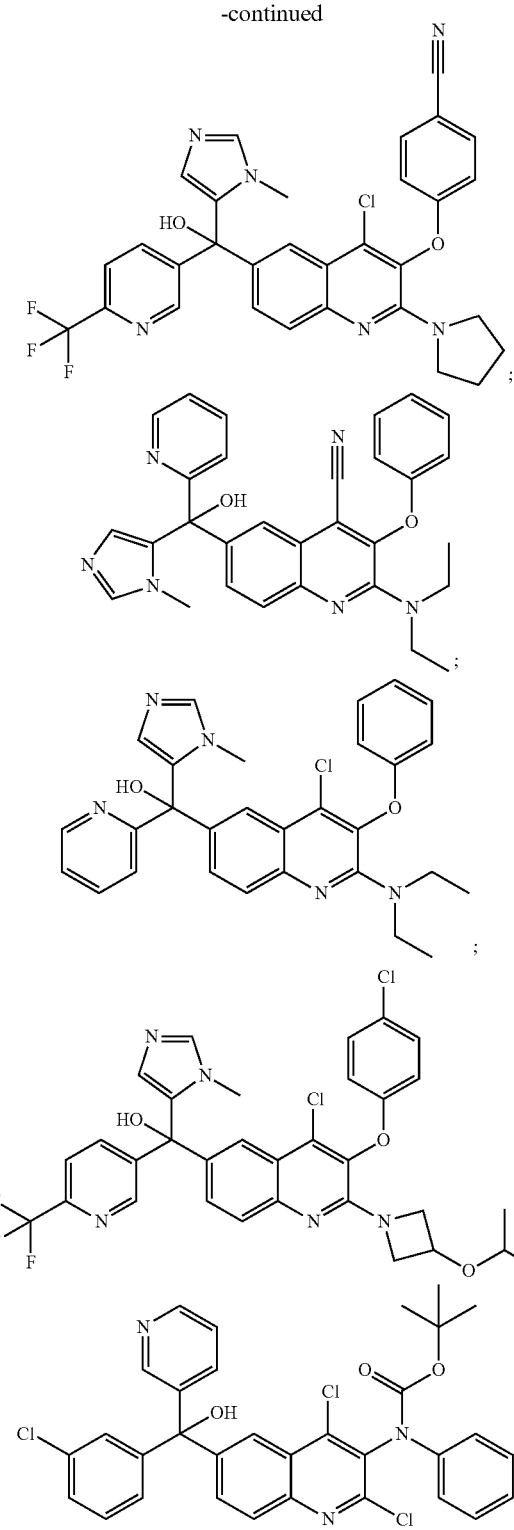

and pharmaceutically acceptable salts thereof.

4. A pharmaceutical composition, comprising a compound of claim 1 and a pharmaceutically acceptable carrier.

5. A pharmaceutical composition made by mixing a compound of claim 1 and a pharmaceutically acceptable carrier.

* * * * *

SEQUENCE LISTING

<160> NUMBER OF SEQ ID NOS: 9

<210> SEQ ID NO 1
<211> LENGTH: 3054
<212> TYPE: DNA
<213> ORGANISM: Homo sapiens

<400> SEQUENCE: 1

```
agagagctag gtgcagagct tcaggctgag gcgctgctga gagggcctcg ccccgcctct      60
gccgccagct gcaccccact cctgaccac ccctgctga aaggacagg gagccaaggc        120
cggcagagcc aaggctcagt catgagaaca caaattgaag tgatcccttg caaaatctgt    180
ggggacaagt cgtctgggat ccactacggg gttatcacct gtgaggggtg caagggcttc    240
ttccgccgga gccagcgctg taacgcggcc tactcctgca cccgtcagca gaactgcccc    300
atcgaccgca ccagccgaaa ccgatgccag cactgccgcc tgcagaaatg cctggcgctg    360
ggcatgtccc gagatgctgt caagttcggc cgcatgtcca agaagcagag ggacagcctg    420
catgcagaag tgcagaaaca gctgcagcag cggcaacagc agcaacagga accagtggtc    480
aagacccctc cagcagggc caaggagca gataccctca cctacacctt ggggctccca     540
gacgggcagc tgccctgggc ctcctcgcct gacctgcctg aggcttctgc ctgtccccct    600
ggcctcctga agcctcagg ctctgggcc tcatattcca caacttggc caaggcaggg      660
ctcaatgggg cctcatgcca ccttgaatac agccctgagc ggggcaaggc tgagggcaga    720
gagagcttct atagcacagg cagccagctg accctgacc gatgtggact tcgttttgag    780
gaacacaggc atcctgggct tggggaactg ggacagggcc cagacagcta cggcagcccc    840
agtttccgca gcacaccgga ggcacccat gcctccctga cagagataga gcacctggtg    900
cagagcgtct gcaagtccta cagggagaca tgccagctgc ggctggagga cctgctgcgg    960
cagcgctcca acatcttctc ccgggaggaa gtgactggct accagaggaa gtccatgtgg   1020
gagatgtggg aacggtgtgc ccaccacctc accgaggcca ttcagtacgt ggtggagttc   1080
gccaagaggc tctcaggctt tatggagctc tgccagaatg accagattgt gcttctcaaa   1140
gcaggagcaa tggaagtggt gctggttagg atgtgccggg cctacaatgc tgacaaccgc   1200
acggtctttt ttgaaggcaa atacggtggc atggagctgt tccgagcctt gggctgcagc   1260
gagctcatca gctccatctt tgacttctcc cactccctaa gtgccttgca ctttccgag    1320
gatgagattg ccctctacac agccttgtt ctcatcaatg cccatcggcc agggctccaa    1380
gagaaaagga agtagaaca gctgcagtac aatctggagc tggcctttca tcatcatctc   1440
tgcaagactc atcgccaaag catcctggca agctgccac caagggaa gcttcggagc     1500
ctgtgtagcc agcatgtgga aaggctgcag atcttccagc acctccaccc catcgtggtc   1560
caagccgctt ccctccact ctacaaggag ctcttcagca ctgaaaccga gtcacctgtg   1620
gggctgtcca agtgacctgg aagagggact ccttgcctct ccctatggcc tgctggccca   1680
cctccctgga ccccgttcca ccctcaccct tttcctttcc catgaaccct ggagggtggt   1740
ccccaccagc tctttggaag tgagcagatg ctgcggctgc ctttctgtca gcaggccggc   1800
ctggcagtgg gacaatcgcc agagggtggg gctggcagaa caccatctcc agcctcagct   1860
ttgacctgtc tcatttccca tattccttca cacccagctt ctgaaggca tggggtggct   1920
gggatttaag gacttctggg ggaccaagac atcctcaaga aaacaggggc atccagggct   1980
ccctggatga atagaatgca attcattcag aagctcagaa gctaagaata agcctttgaa   2040
atacctcatt gcatttccct ttgggcttcg gcttgggag atggatcaag ctcagagact    2100
```

```
ggcagtgaga gcccagaagg acctgtataa aatgaatctg gagctttaca ttttctgcct    2160
ctgccttcct cccagctcag caaggaagta tttgggcacc ctacccttta cctggggtct    2220
aaccaaaaat ggatgggatg aggatgagag gctggagata attgttttat gggatttggg    2280
tgtgggacta gggtacaatg aaggccaaga gcatctcaga catagagtta aaactcaaac    2340
ctcttatgtg cactttaaag atagacttta ggggctggca caaatctgat cagagacaca    2400
tatccataca caggtgaaac acatacagac tcaacagcaa tcatgcagtt ccagagacac    2460
atgaacctga cacaatctct cttatccttg aggccacagc ttggaggagc tagaggcct     2520 caggggaaag tcccaatcct gagggaccct cccaaacatt tccatggtgc tccagtccac    2580
tgatcttggg tctggggtga tccaaatacc accccagctc cagctgtctt ctaccactag    2640
aagacccaag agaagcagaa gtcgctcgca ctggtcagtc ggaaggcaag atcagatcct    2700
ggaggacttt cctggcctgc ccgccagccc tgctcttgtt gtggagaagg aagcagatgt    2760
gatcacatca ccccgtcatt gggcaccgct gactccagca tggaggacac cagggagcag    2820
ggcctgggcc tgtttcccca gctgtgatct tgcccagaac ctctcttggc ttcataaaca    2880
gctgtgaacc ctcccctgag ggattaacag caatgatggg cagtcgtgga gttggggggg    2940
ttgggggtgg gattgtgtcc tctaagggga cgggttcatc tgagtaaaca taaaccccaa    3000
cttgtgccat tctttataaa atgatttta aggcaaaaaa aaaaaaaaa aaaa            3054

<210> SEQ ID NO 2
<211> LENGTH: 786
<212> TYPE: DNA
<213> ORGANISM: Homo sapiens

<400> SEQUENCE: 2
agcacaccgg aggcacccta tgcctccctg acagagatag agcacctggt gcagagcgtc     60
tgcaagtcct acagggagac atgccagctg cggctggagg acctgctgcg gcagcgctcc    120
aacatcttct cccgggagga agtgactggc taccagagga agtccatgtg ggagatgtgg    180
gaacggtgtg cccaccacct caccgaggcc attcagtacg tggtggagtt cgccaagagg    240
ctctcaggct ttatggagct ctgccagaat gaccagattg tgcttctcaa agcaggagca    300
atggaagtgg tgctggttag gatgtgccgg gcctacaatg ctgacaaccg cacggtcttt    360
tttgaaggca aatacggtgg catggagctg ttccgagcct tgggctgcag cgagctcatc    420
agctccatct ttgacttctc ccactcccta agtgccttgc acttttccga ggatgagatt    480
gccctctaca cagcccttgt tctcatcaat gcccatcggc cagggctcca agagaaaagg    540
aaagtagaac agctgcagta caatctggag ctggcctttc atcatcatct ctgcaagact    600
catcgccaaa gcatcctggc aaagctgcca cccaagggga agcttcggag cctgtgtagc    660
cagcatgtgg aaaggctgca gatcttccag cacctccacc ccatcgtggt ccaagccgct    720
ttccctccac tctacaagga gctcttcagc actgaaaccg agtcacctgt ggggctgtcc    780
aagtga                                                                786

<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3
```

```
Glu Asn Leu Tyr Phe Gln Gly
1               5
```

<210> SEQ ID NO 4
<211> LENGTH: 283
<212> TYPE: PRT
<213> ORGANISM: Artificial Sequence
<220> FEATURE:
<223> OTHER INFORMATION: Construct used in the Thermofluor assay

<400> SEQUENCE: 4

```
Met Ala His His His His His Ala Gly Ala Glu Asn Leu Tyr
1               5                   10                  15

Phe Gln Gly Ala Met Asp Ser Thr Pro Glu Ala Pro Tyr Ala Ser Leu
            20                  25                  30

Thr Glu Ile Glu His Leu Val Gln Ser Val Cys Lys Ser Tyr Arg Glu
        35                  40                  45

Thr Cys Gln Leu Arg Leu Glu Asp Leu Leu Arg Gln Arg Ser Asn Ile
    50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95

Val Glu Phe Ala Lys Arg Leu Ser Gly Phe Met Glu Leu Cys Gln Asn
            100                 105                 110

Asp Gln Ile Val Leu Leu Lys Ala Gly Ala Met Glu Val Val Leu Val
        115                 120                 125

Arg Met Cys Arg Ala Tyr Asn Ala Asp Asn Arg Thr Val Phe Phe Glu
    130                 135                 140

Gly Lys Tyr Gly Gly Met Glu Leu Phe Arg Ala Leu Gly Cys Ser Glu
145                 150                 155                 160

Leu Ile Ser Ser Ile Phe Asp Phe Ser His Ser Leu Ser Ala Leu His
                165                 170                 175

Phe Ser Glu Asp Glu Ile Ala Leu Tyr Thr Ala Leu Val Leu Ile Asn
            180                 185                 190

Ala His Arg Pro Gly Leu Gln Glu Lys Arg Lys Val Glu Gln Leu Gln
        195                 200                 205

Tyr Asn Leu Glu Leu Ala Phe His His Leu Cys Lys Thr His Arg
    210                 215                 220

Gln Ser Ile Leu Ala Lys Leu Pro Pro Lys Gly Lys Leu Arg Ser Leu
225                 230                 235                 240

Cys Ser Gln His Val Glu Arg Leu Gln Ile Phe Gln His Leu His Pro
                245                 250                 255

Ile Val Val Gln Ala Ala Phe Pro Pro Leu Tyr Lys Glu Leu Phe Ser
            260                 265                 270

Thr Glu Thr Glu Ser Pro Val Gly Leu Ser Lys
        275                 280
```

<210> SEQ ID NO 5
<211> LENGTH: 6
<212> TYPE: PRT
<213> ORGANISM: Homo sapiens

<400> SEQUENCE: 5

```
Leu Tyr Lys Glu Leu Phe
1               5
```

<210> SEQ ID NO 6
<211> LENGTH: 6
<212> TYPE: PRT
<213> ORGANISM: Artificial Sequence
<220> FEATURE:
<223> OTHER INFORMATION: mutated AF2 domain

<400> SEQUENCE: 6

Leu Phe Lys Glu Leu Phe
1               5

<210> SEQ ID NO 7
<211> LENGTH: 786
<212> TYPE: DNA
<213> ORGANISM: Artificial Sequence
<220> FEATURE:
<223> OTHER INFORMATION: LBD with mutated AF2 domain

<400> SEQUENCE: 7

```
agcacaccgg aggcacccta tgcctccctg acagagatag agcacctggt gcagagcgtc      60
tgcaagtcct acagggagac atgccagctg cggctggagg acctgctgcg gcagcgctcc     120
aacatcttct cccggggagga agtgactggc taccagagga agtccatgtg ggagatgtgg    180
gaacggtgtg cccaccacct caccgaggcc attcagtacg tggtggagtt cgccaagagg    240
ctctcaggct ttatggagct ctgccagaat gaccagattg tgcttctcaa agcaggagca    300
atggaagtgg tgctggttag gatgtgccgg gcctacaatg ctgacaaccg cacggtcttt    360
tttgaaggca aatacggtgg catggagctg ttccgagcct gggctgcag cgagctcatc     420 agctccatct ttgacttctc ccactcccta agtgccttgc acttttccga ggatgagatt    480
gccctctaca cagcccttgt tctcatcaat gcccatcggc agggctcca agagaaaagg     540 aaagtagaac agctgcagta caatctggag ctggccttc atcatcatct ctgcaagact     600
catcgccaaa gcatcctggc aaagctgcca cccaagggga agcttcggag cctgtgtagc    660
cagcatgtgg aaaggctgca gatcttccag cacctccacc ccatcgtggt ccaagccgct    720
ttccctccac tcttcaagga gctcttcagc actgaaaccg agtcacctgt ggggctgtcc    780
aagtga                                                                786
```

<210> SEQ ID NO 8
<211> LENGTH: 261
<212> TYPE: PRT
<213> ORGANISM: Homo sapiens

<400> SEQUENCE: 8

Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

```
Asn Ala Asp Asn Arg Thr Val Phe Phe Glu Gly Lys Tyr Gly Gly Met
            115                 120                 125

Glu Leu Phe Arg Ala Leu Gly Cys Ser Glu Leu Ile Ser Ser Ile Phe
130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
            165                 170                 175

Gln Glu Lys Arg Lys Val Glu Gln Leu Gln Tyr Asn Leu Glu Leu Ala
            180                 185                 190

Phe His His His Leu Cys Lys Thr His Arg Gln Ser Ile Leu Ala Lys
            195                 200                 205

Leu Pro Pro Lys Gly Lys Leu Arg Ser Leu Cys Ser Gln His Val Glu
            210                 215                 220

Arg Leu Gln Ile Phe Gln His Leu His Pro Ile Val Val Gln Ala Ala
225                 230                 235                 240

Phe Pro Pro Leu Tyr Lys Glu Leu Phe Ser Thr Glu Thr Glu Ser Pro
            245                 250                 255

Val Gly Leu Ser Lys
            260

<210> SEQ ID NO 9
<211> LENGTH: 261
<212> TYPE: PRT
<213> ORGANISM: Artificial Sequence
<220> FEATURE:
<223> OTHER INFORMATION: LBD with mutated AF2 domain

<400> SEQUENCE: 9

Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
            35                  40                  45

Thr Gly Tyr Gln Arg Lys Ser Met Trp Glu Met Trp Glu Arg Cys Ala
50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
            85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
            115                 120                 125

Glu Leu Phe Arg Ala Leu Gly Cys Ser Glu Leu Ile Ser Ser Ile Phe
130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
            165                 170                 175

Gln Glu Lys Arg Lys Val Glu Gln Leu Gln Tyr Asn Leu Glu Leu Ala
            180                 185                 190

Phe His His His Leu Cys Lys Thr His Arg Gln Ser Ile Leu Ala Lys
            195                 200                 205
```

```
Leu Pro Pro Lys Gly Lys Leu Arg Ser Leu Cys Ser Gln His Val Glu
    210             215                 220
Arg Leu Gln Ile Phe Gln His Leu His Pro Ile Val Val Gln Ala Ala
225             230                 235                 240
Phe Pro Pro Leu Phe Lys Glu Leu Phe Ser Thr Glu Thr Glu Ser Pro
                245                 250                 255
Val Gly Leu Ser Lys
            260
```